US006297037B1

(12) United States Patent
Barnett et al.

(10) Patent No.: US 6,297,037 B1
(45) Date of Patent: *Oct. 2, 2001

(54) OXIDATIVELY STABLE ALPHA-AMYLASE

(76) Inventors: Christopher C. Barnett, 63 Highland Ave., South San Francisco, CA (US) 94080; Colin Mitchinson, 381 Myrtle St., Half Moon Bay, CA (US) 94019; Scott D. Power, 732 Olive Ct., San Bruno, CA (US) 94066; Carol A. Requadt, 4094 Paradise Dr., Tiburon, CA (US) 94920

( * ) Notice: Subject to any disclaimer, the term of this patent is extended or adjusted under 35 U.S.C. 154(b) by 0 days.

This patent is subject to a terminal disclaimer.

(21) Appl. No.: 08/194,664

(22) Filed: Feb. 10, 1994

Related U.S. Application Data

(63) Continuation-in-part of application No. 08/016,395, filed on Feb. 11, 1993, now abandoned.

(51) Int. Cl.[7] .............................. C12N 9/28; C12N 15/56

(52) U.S. Cl. ........................ 435/202; 435/201; 435/203; 435/274; 435/275; 435/172.3; 435/471; 435/485; 252/174.21; 252/DIG. 12

(58) Field of Search ................................. 435/201, 202, 435/203, 172.3, 274, 275, 471, 485; 536/23.2; 252/174.12, DIG. 12; 510/306, 392

(56) References Cited

U.S. PATENT DOCUMENTS

| 4,261,868 | 4/1981 | Hora et al. ............................ 252/529 |
| 4,284,722 | 8/1981 | Tamuri et al. ......................... 435/94 |
| 4,493,893 | 1/1985 | Mielenz et al. .................... 435/172.3 |
| 4,620,936 | 11/1986 | Kielman et al. ........................ 252/99 |
| 4,634,551 | 1/1987 | Burns et al. .......................... 252/102 |
| 4,760,025 | 7/1988 | Estell .................................... 435/222 |

FOREIGN PATENT DOCUMENTS

| 0946/92 | 7/1992 | (DK) . |
| 1503/92 | 12/1992 | (DK) . |
| 0 130 756 | 1/1985 | (EP) . |
| 0285123 | * 10/1988 | (EP) . |
| 0 378 261 | 7/1990 | (EP) . |
| 0 409 299 A2 | 1/1991 | (EP) . |
| 0 410 498 A2 | 1/1991 | (EP) . |
| 2 676 456 | 11/1992 | (FR) . |
| WO 91/00353 | 1/1991 | (WO) . |
| WO 91/16423 | 10/1991 | (WO) . |
| 92/08778 | 5/1992 | (WO) . |
| 9402597 | * 2/1994 | (WO) . |
| WO 94/02597 | 2/1994 | (WO) . |

OTHER PUBLICATIONS

Declerck, et al., "Use of Amber Suppressors to Investigate the Thermostability of *Bacillus licheniformis* α–Amylase" *J. of Biol. Chem.* 265(26):15481–15488 (1990).

Manning, et al., "Thermostable α–Amylase of *Bacillus stearothermophilus*" *J. of Biol. Chem.* 236(11):2952–2965 (Nov. 1961).

Matsui, et al., "A mutant α–amylase with enhanced activity specific for short substrates" *FEBS 11596* 310(3):216–218 (Oct. 1992).

Nakajima, et al., "Nucleotide Sequence of the *Bacillus stearothermophilus* α–Amylase Gene" *J. Bacteriology* 163(1):401–406 (Jul. 1985).

Ogasahara, et al., "Studies on Thermophilic α–Amylase from *Bacillus stearothermophilus*" *J. Biochem.* 67(1):65–89 (1970).

Ottesen et al., "The Subtilisins" *Methods in Enzymology* 19:199–215 (1970).

Takase et al., "Site–directed mutagenesis of active site residues in *Bacillus subtilis* a–amylase" *Biochimica et Biophysica Acta* 1120–281–288 (1992).

Bealin–Kelly et al, "Studies on the thermostability of the alpha–amylase of *bacillus–caldovelox*" *Appl. Microbiol. and Biotech* 36(3):332–336 (Dec. 1991).

Estell, et al., "Engineering an Enzyme by sitedirected Mutagenesis to Be Resistant to Chemical Oxidation" *J. Biol. Chem.* 260(11):6518–6521 (Jun. 1985).

Brosnan, et al., "Investigation of the mechanism of irreversible thermoinactivation of *bacillus–stearothermophilu* alpha–amylase" *Eur. J. Biotech.* 203(1–2):225–231 (Jan. 1992).

Joyet, P., et al., biotechnology, vol. 10, Dec. 1992, pp. 1579–1583.

Janecek, FEBS 11085, vol. 304, No. 1,1–3 (Jun. 1992.

Holm, L., et al., Protein Engineering, vol. 3, No. 3, pp. 181–191, 1990.

Suzuki, Y., et al., The Journal of Biological Chemistry, vol. 264, No. 32, pp. 18933–18938 (1989.

Vihinen, M., et al., J. Biochem, 107, pp. 267–272 (1990).

Nakajima, R., et al., Journal of Bacteriology, Jul. 1985, pp. 401–406.

Tomazic, S.J., et al., The Journal of Biological Chemistry, vol. 263, No. 7, pp. 3086–3096, 1988.

Gray, G.L., et al., Journal of Bacteriology, vol. 166, No. 2, 1986, pp. 635–643.

(List continued on next page.)

*Primary Examiner*—Robert A. Wax
*Assistant Examiner*—Rebecca Prouty

(57) ABSTRACT

Novel alpha-amylase mutants derived from the DNA sequences of naturally occurring or recombinant alpha-amylases are disclosed. The mutant alpha-amylases, in general, are obtained by in vitro modifications of a precursor DNA sequence encoding the naturally occurring or recombinant alpha-amylase to generate the substitution (replacement) or deletion of one or more oxidizable amino acid residues in the amino acid sequence of a precursor alpha-amylase. Such mutant alpha-amylases have altered oxidative stability and/or altered pH performance profiles and/or altered thermal stability as compared to the precursor. Also disclosed are detergent and starch liquefaction compositions comprising the mutant amylases, as well as methods of using the mutant amylases.

25 Claims, 22 Drawing Sheets

OTHER PUBLICATIONS

Jorgensen, P.L., et al., FEMS Microbiology Letters 77 (1991) pp. 271–276.

B. Svensson et al. "Mutational Analysis of Glycosylase Function" J. Biotechnol. 29: 1–37 (1993).*

M. Søgaard et al. "Site–directed Mutagenesis of Histidine 93. . ." J. Biol. Chem. 268(30)22480–22484 (Oct. 1993).*

I. Matsui et al. "An Increase in the Transglycosylation Activity" Biochim. Biophys. Acta. 1077:416–419 (1991).*

L. Holm. et al. "Random Mutagenesis Used to Probe the Structure. . ." Prot. Eng. 3(3) 181–191 (1990).*

* cited by examiner

```
                  10                       30                        50
AGCTTGAAGAAGTGAAGAAGCAGAGAGGCTATTGAATAAATGAGTAGAAAGCGCCATATC 70                       90                       110
GGCGCTTTTCTTTTGGAAGAAAATATAGGGAAAATGGTACTTGTTAAAAATTCGGAATAT 130                      150                       170
TTATACAACATCATATGTTTCACATTGAAAGGGGAGGAGAATCATGAAACAACAAAAACG
                                                  M   K   Q   Q   K   R
                 190                      210                       230
GCTTTACGCCCGATTGCTGACGCTGTTATTTGCGCTCATCTTCTTGCTGCCTCATTCTGC
  L   Y   A   R   L   L   T   L   L   F   A   L   I   F   L   L   P   H   S   A
                 250                      270                       290
AGCAGCGGCGGCAAATCTTAATGGGACGCTGATGCAGTATTTTGAATGGTACATGCCCAA
  A   A   A   A   N   L   N   G   T   L   M   Q   Y   F   E   W   Y   M   P   N
                 310                      330                       350
TGACGGCCAACATTGGAAGCGTTTGCAAAACGACTCGGCATATTTGGCTGAACACGGTAT
  D   G   Q   H   W   K   R   L   Q   N   D   S   A   Y   L   A   E   H   G   I
                 370                      390                       410
TACTGCCGTCTGGATTCCCCCGGCATATAAGGGAACGAGCCAAGCGGATGTGGGCTACGG
  T   A   V   W   I   P   P   A   Y   K   G   T   S   Q   A   D   V   G   Y   G
                 430                      450                       470
TGCTTACGACCTTTATGATTTAGGGGAGTTTCATCAAAAAGGGACGGTTCGGACAAAGTA
  A   Y   D   L   Y   D   L   G   E   F   H   Q   K   G   T   V   R   T   K   Y
                 490                      510                       530
CGGCACAAAAGGAGAGCTGCAATCTGCGATCAAAAGTCTTCATTCCCGCGACATTAACGT
  G   T   K   G   E   L   Q   S   A   I   K   S   L   H   S   R   D   I   N   V
                 550                      570                       590
TTACGGGGATGTGGTCATCAACCACAAAGGCGGCGCTGATGCGACCGAAGATGTAACCGC
  Y   G   D   V   V   I   N   H   K   G   G   A   D   A   T   E   D   V   T   A
                 610                      630                       650
GGTTGAAGTCGATCCCGCTGACCGCAACCGCGTAATTTCAGGAGAACACCTAATTAAAGC
  V   E   V   D   P   A   D   R   N   R   V   I   S   G   E   H   L   I   K   A
                 670                      690                       710
CTGGACACATTTTCATTTTCCGGGGCGCGGCAGCACATACAGCGATTTTAAATGGCATTG
  W   T   H   F   H   F   P   G   R   G   S   T   Y   S   D   F   K   W   H   W
                 730                      750                       770
GTACCATTTTGACGGAACCGATTGGGACGAGTCCCGAAAGCTGAACCGCATCTATAAGTT
  Y   H   F   D   G   T   D   W   D   E   S   R   K   L   N   R   I   Y   K   F
                 790                      810                       830
TCAAGGAAAGGCTTGGGATTGGGAAGTTTCCAATGAAAACGGCAACTATGATTATTTGAT
  Q   G   K   A   W   D   W   E   V   S   N   E   N   G   N   Y   D   Y   L   M
```

FIG. 1A

```
           850                 870                 890
GTATGCCGACATCGATTATGACCATCCTGATGTCGCAGCAGAAATTAAGAGATGGGGCAC
 Y   A   D   I   D   Y   D   H   P   D   V   A   A   E   I   K   R   W   G   T
           910                 930                 950
TTGGTATGCCAATGAACTGCAATTGGACGGTTTCCGTCTTGATGCTGTCAAACACATTAA
 W   Y   A   N   E   L   Q   L   D   G   F   R   L   D   A   V   K   H   I   K
           970                 990                1010
ATTTTCTTTTTTGCGGGATTGGGTTAATCATGTCAGGGAAAAAACGGGGAAGGAAATGTT
 F   S   F   L   R   D   W   V   N   H   V   R   E   K   T   G   K   E   M   F
          1030                1050                1070
TACGGTAGCTGAATATTGGCAGAATGACTTGGGCGCGCTGGAAAACTATTTGAACAAAAC
 T   V   A   E   Y   W   Q   N   D   L   G   A   L   E   N   Y   L   N   K   T
          1090                1110                1130
AAATTTTAATCATTCAGTGTTTGACGTGCCGCTTCATTATCAGTTCCATGCTGCATCGAC
 N   F   N   H   S   V   F   D   V   P   L   H   Y   Q   F   H   A   A   S   T
          1150                1170                1190
ACAGGGAGGCGGCTATGATATGAGGAAATTGCTGAACGGTACGGTCGTTTCCAAGCATCC
 Q   G   G   G   Y   D   M   R   K   L   L   N   G   T   V   V   S   K   H   P
          1210                1230                1250
GTTGAAATCGGTTACATTTGTCGATAACCATGATACACAGCCGGGGCAATCGCTTGAGTC
 L   K   S   V   T   F   V   D   N   H   D   T   Q   P   G   Q   S   L   E   S
          1270                1290                1310
GACTGTCCAAACATGGTTTAAGCCGCTTGCTTACGCTTTTATTCTCACAAGGGAATCTGG
 T   V   Q   T   W   F   K   P   L   A   Y   A   F   I   L   T   R   E   S   G
          1330                1350                1370
ATACCCTCAGGTTTTCTACGGGGATATGTACGGGACGAAAGGAGACTCCCAGCGCGAAAT
 Y   P   Q   V   F   Y   G   D   M   Y   G   T   K   G   D   S   Q   R   E   I
          1390                1410                1430
TCCTGCCTTGAAACACAAAATTGAACCGATCTTAAAAGCGAGAAAACAGTATGCGTACGG
 P   A   L   K   H   K   I   E   P   I   L   K   A   R   K   Q   Y   A   Y   G
          1450                1470                1490
AGCACAGCATGATTATTTCGACCACCATGACATTGTCGGCTGGACAAGGGAAGGCGACAG
 A   Q   H   D   Y   F   D   H   H   D   I   V   G   W   T   R   E   G   D   S
          1510                1530                1550
CTCGGTTGCAAATTCAGGTTTGGCGGCATTAATAACAGACGGACCCGGTGGGGCAAAGCG
 S   V   A   N   S   G   L   A   A   L   I   T   D   G   P   G   G   A   K   R
          1570                1590                1610
AATGTATGTCGGCCGGCAAAACGCCGGTGAGACATGGCATGACATTACCGGAAACCGTTC
 M   Y   V   G   R   Q   N   A   G   E   T   W   H   D   I   T   G   N   R   S
          1630                1650                1670
GGAGCCGGTTGTCATCAATTCGGAAGGCTGGGGAGAGTTTCACGTAAACGGCGGGTCGGT
 E   P   V   V   I   N   S   E   G   W   G   E   F   H   V   N   G   G   S   V
```

*FIG._1B*

```
                1690              1710              1730
TTCAATTTATGTTCAAAGATAGAAGAGCAGAGAGGACGGATTTCCTGAAGGAAATCCGTT
  S   I   Y   V   Q   R   *
                1750              1770              1790
TTTTTATTTTGCCCGTCTTATAAATTTCTTTGATTACATTTTATAATTAATTTTAACAAA 1810              1830              1850
GTGTCATCAGCCCTCAGGAAGGACTTGCTGACAGTTTGAATCGCATAGGTAAGGCGGGGA 1870              1890              1910
TGAAATGGCAACGTTATCTGATGTAGCAAAGAAAGCAAATGTGTCGAAAATGACGGTATC 1930              1950
GCGGGTGATCAATCATCCTGAGACTGTGACGGATGAATTGAAAAAGCT
```

FIG._1C

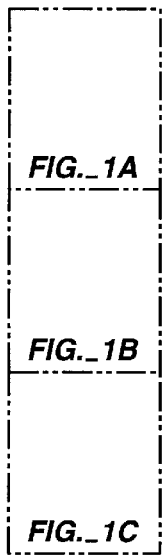

FIG._1

```
          10                  30                  50
ANLNGTLMQYFEWYMPNDGQHWKRLQNDSAYLAEHGITAVWIPPAYKGTSQADVGYGAYD 70                  90                 110
LYDLGEFHQKGTVRTKYGTKGELQSAIKSLHSRDINVYGDVVINHKGGADATEDVTAVEV 130                 150                 170
DPADRNRVISGEHLIKAWTHFHFPGRGSTYSDFKWHWYHFDGTDWDESRKLNRIYKFQGK 190                 210                 230
AWDWEVSNENGNYDYLMYADIDYDHPDVAAEIKRWGTWYANELQLDGFRLDAVKHIKFSF 250                 270                 290
LRDWVNHVREKTGKEMFTVAEYWQNDLGALENYLNKTNFNHSVFDVPLHYQFHAASTQGG 310                 330                 350
GYDMRKLLNGTVVSKHPLKSVTFVDNHDTQPGQSLESTVQTWFKPLAYAFILTRESGYPQ 370                 390                 410
VFYGDMYGTKGDSQREIPALKHKIEPILKARKQYAYGAQHDYFDHHDIVGWTREGDSSVA 430                 450                 470
NSGLAALITDGPGGAKRMYVGRQNAGETWHDITGNRSEPVVINSEGWGEFHVNGGSVSIY

VQR
```

FIG._2

Am-Lich = B.Licheniformis    Am-Amylo = B.amyloliquefaciens    Am-Stearo = B.stearothermophilus

```
           1                                                                        19
                                                                                    60
Am-Lich    .......MKQQ  KRLYARLLTL  LFALIFLLPH  ..........  .......SAAA  AANLNGTLMQ  YFEWYMPNDG
Am-Amylo   MRGRGNMIQK  RKRTVSFRLV  LMCTLLFVSL  ..........  .......PITK  TSAVNGTLMQ  YFEWYTPNDG
Am-Stearo  ..........  .......VLTF  HRIIRKGWMF  LLAFLLTASL  FCPTGRHAKA  AAPFNGTMMQ  YFEWYLPDDG 61                                                                       79
                                                                                    120
Am-Lich    QHWKRLQNDS  AYLAEHGITA  VWIPPAYKGT  SQADVGYGAY  DLYDLGEFHQ  KGTVRTKYGT
Am-Amylo   QHWKRLQNDA  EHLSDIGITA  VWIPPAYKGL  SQSDNGYGPY  DLYDLGEFQQ  KGTVRTKYGT
Am-Stearo  TLWTKVANEA  NNLSSLGITA  LSLPPAYKGT  SRSDVGYGVY  DLYDLGEFNQ  KGTVRTKYGT 121                                                                      139
                                                                                    180
Am-Lich    KGELQSAIKS  LHSRDINVYG  DVVINHKGGA  DATEDVTAVE  VDPADRNRVI  SGEHLIKAWT
Am-Amylo   KSELQDAIGS  LHSRNVQVYG  DVVLNHKAGA  DATEDVTAVE  VNPANRNQET  SEEYQIKAWT
Am-Stearo  KAQYLQAIQA  AHAAGMQVYA  DVVFDHKGGA  DGTEWDAVE   VNPSDRNQEI  SGTYQIQAWT 181                                                                      197
                                                                                    240
Am-Lich    HFHFPGRGST  YSDFKWHWYH  FDGTDWDESR  KLNRIYKF...  FRLDAVKHIK  QGKAWDWEVS  NENGNYDYLM
Am-Amylo   DFRFPGRGNT  YSDFKWHWYH  FDGADWDESR  KISRIFKFRG   FRIDAAKHIK  EGKAWDWEVS  SENGNYDYLM
Am-Stearo  KFDFPGRGNT  YSSFKWRWYH  FDGVDWDESR  KLSRIYKFRG   FRLDGLKHIK  IGKAWDWEVD  TENGNYDYLM 241                                                                      257
                                                                                    300
Am-Lich    YADIDYDHPD  VAAEIKRWGT  WYANELQLDG  GALENYLNKT  NFNHSVFDVP  LHYQFHAAST  VREKTGKEMF
Am-Amylo   YADVDYDHPD  VVAETKKWGI  WYANELSLDG  GKLENYLNKT  SFNQSVFDVP  LHFNLQAASS  VRQATGKEMF
Am-Stearo  YADLDMDHPE  VVTELKNWGK  WYVNTTNIDG  NKLHNYITKT  NGTMSLFDAP  LHNKFYTASK  VRSQTGKPLF 301                                                                      317
                                                                                    360
Am-Lich    TVAEYWQNDL  GALENYLNKT  NFNHSVFDVP  LHYQFHAAST  QGGGYDMRKL  LNGTVVSKHP
Am-Amylo   TVAEYWQNNA  GKLENYLNKT  SFNQSVFDVP  LHFNLQAASS  QGGGYDMRRL  LDGTVVSRHP
Am-Stearo  TVGEYWSYDI  NKLHNYITKT  NGTMSLFDAP  LHNKFYTASK  SGGAFDMRTL  MTNTLMKDQP
```

FIG._3A

```
            361
Am-Lich     LKSVTFVDNH DTQPGQSLES TVQTWFKPLA YAFILTRESG YPQVFYGDMY GTKGDSQREI    377
Am-Amylo    EKAVTFVENH DTQPGQSLES TVQTWFKPLA YAFILTRESG YPQVFYGDMY GTKGTSPKEI    420
Am-Stearo   TLAVTFVDNH DTNPAKR..CS HGRPWFKPLA YAFILTRQEG YPCVFYGDYY GI.....PQYNI 421
Am-Lich     PALKHKIEPI LKARKQYAYG AQHDYFDHHD IVGWTREGDS SVANSGLAAL ITDGPGGAKR    437
Am-Amylo    PSLKDNIEPI LKARKEYAYG PQHDYIDHPD VIGWTREGDS SAAKSGLAAL ITDGPGGSKR    480
Am-Stearo   PSLKSKIDPL LIARRDYAYG TQHDYLDHSD IIGWTREGVT EKPGSGLAAL ITDGAGRSKW 481                                               483
Am-Lich     MYVGRQNAGE TWHDITGNRS EPVVINSEGW GEFHVNGGSV SIYVQR........             540
Am-Amylo    MYAGLKNAGE TWYDITGNRS DTVKIGSDGW GEFHVNDGSV SIYVQK........
Am-Stearo   MYVGKQHAGK VFYDLTGNRS DTVTINSDGW GEFKVNGGSV SVWVPRKTTV STIARPITTR 541                                   559
Am-Lich     ............ ............
Am-Amylo    ............ ............
Am-Stearo   PWTGEFVRWH EPRLVAWP*
```

| FIG._3A |
| FIG._3B |

```
          10                      30                      50
ANLNGTLMQYFEWYMPNDGQHWKRLQNDSAYLAEHGITAVWIPPAYKGTSQADVGYGAYD 70                      90                     110
LYDLGEFHQKGTVRTKYGTKGELQSAIKSLHSRDINVYGDVVINHKGGADATEDVTAVEV 130                     150                     170
DPADRNRVISGEHLIKAWTHFHFPGRGSTYSDFKWHWYHFDGTDWDESRKLNRIYKFQGK 190                     210                     230
AWDWEVSNENGNYDYLTYADIDYDHPDVAAEIKRWGTWYANELQLDGFRLDAVKHIKFSF 250                     270                     290
LRDWVNHVREKTGKEMFTVAEYWQNDLGALENYLNKTNFNHSVFDVPLHYQFHAASTQGG 310                     330                     350
GYDMRKLLNGTVVSKHPLKSVTFVDNHDTQPGQSLESTVQTWFKPLAYAFILTRESGYPQ 370                     390                     410
VFYGDMYGTKGDSQREIPALKHKIEPILKARKQYAYGAQHDYFDHHDIVGWTREGDSSVA 430                     450                     470
NSGLAALITDGPGGAKRMYVGRQNAGETWHDITGNRSEPVVINSEGWGEFHVNGGSVSIY

VQR
```

FIG._4a

```
                                                              AAAA
           14                  34                  54
ANLNGTLMQYFEWYMPNDGQHWKRLQNDSAYLAEHGITAVWIPPAYKGTSQADVGYGAYD 74                  94                 114
LYDLGEFHQKGTVRTKYGTKGELQSAIKSLHSRDINVYGDVVINHKGGADATEDVTAVEV 134                 154                 174
DPADRNRVISGEHLIKAWTHFHFPGRGSTYSDFKWHWYHFDGTDWDESRKLNRIYKFQGK 194                 214                 234
AWDWEVSNENGNYDYLMYADIDYDHPDVAAEIKRWGTWYANELQLDGFRLDAVKHIKFSF 254                 274                 294
LRDWVNHVREKTGKEMFTVAEYWQNDLGALENYLNKTNFNHSVFDVPLHYQFHAASTQGG 314                 334                 354
GYDMRKLLNGTVVSKHPLKSVTFVDNHDTQPGQSLESTVQTWFKPLAYAFILTRESGYPQ 374                 394                 414
VFYGDMYGTKGDSQREIPALKHKIEPILKARKQYAYGAQHDYFDHHDIVGWTREGDSSVA 434                 454                 474
NSGLAALITDGPGGAKRMYVGRQNAGETWHDITGNRSEPVVINSEGWGEFHVNGGSVSIY

VQR
```

FIG._4b

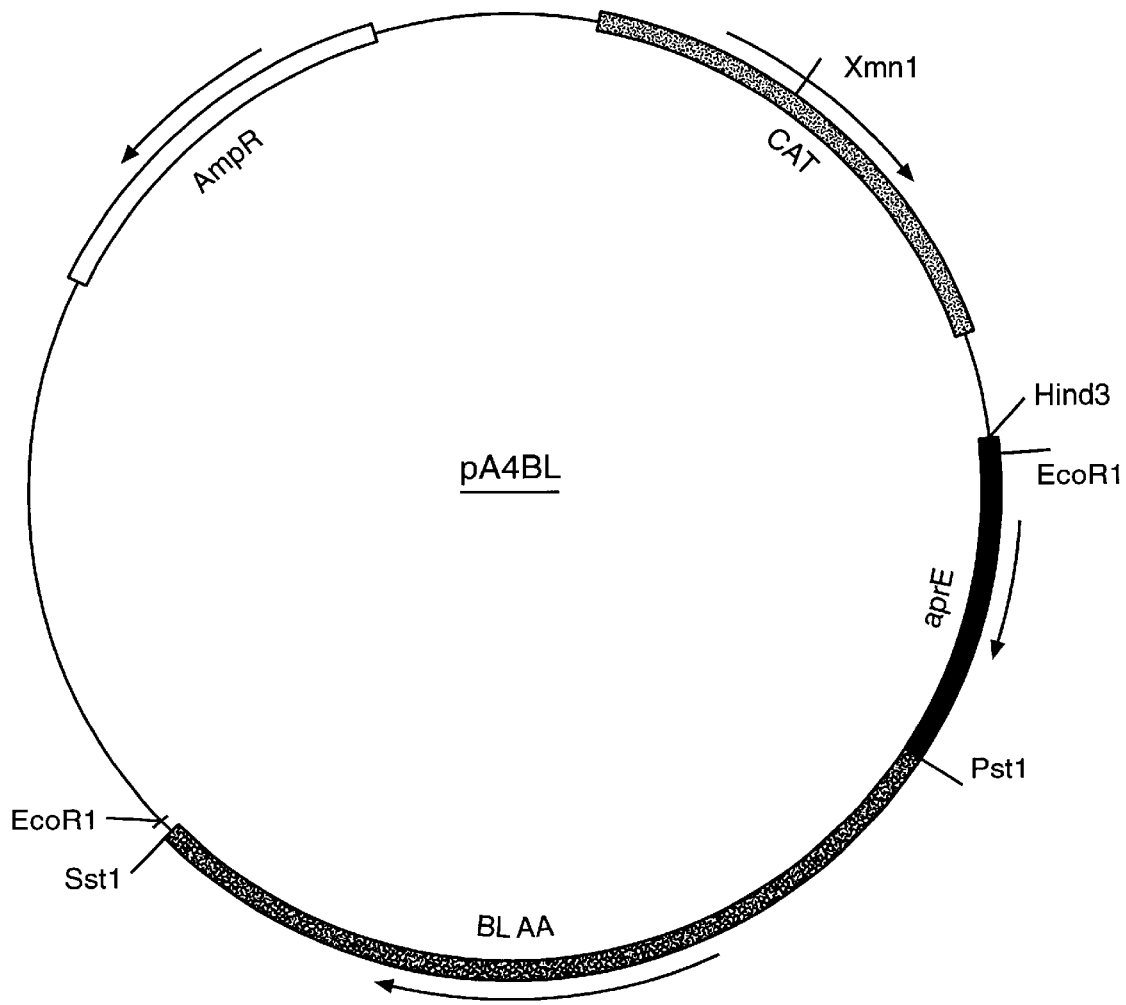
FIG._5

SIGNAL SEQUENCE - MATURE PROTEIN JUNCTIONS IN:

*B.licheniformis* alpha-amylase.                                 (PstI)

M K Q Q K R L T A R L L T L L F A L I F L L P H S A′A A A[A N L......
                                                                                     N-terminus

*B.subtilis* alkaline protease aprE.                               (PstI)

M R S K T L W I S L L F A L T L I F T M A F S N M S A Q A[A′G K S......
                                                                                        N-terminus

*B.licheniformis* alpha-amylase in pA4BL.                     (PstI)

M R S K T L W I S L L F A L T L I F T M A F S N M S A Q A[A′A A A N.
                                                                                      N-terminus

*B.lichenfiormis* alpha-amylase in pBLapr.

M R S K T L W I S L L F A L T L I F T M A F S N M S A Q A[A N L......
                                                                                     N-terminus (PstI)  indicates the site of the restriction site in the gene.

N-terminus    indicates cleavage site between signal peptide and secreted protein.

FIG._6

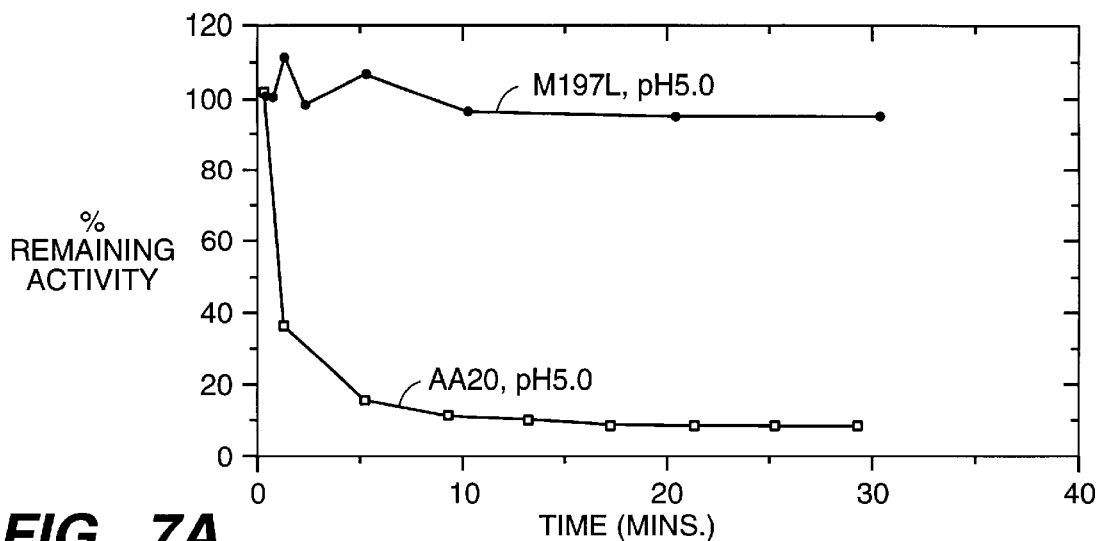
FIG._7A
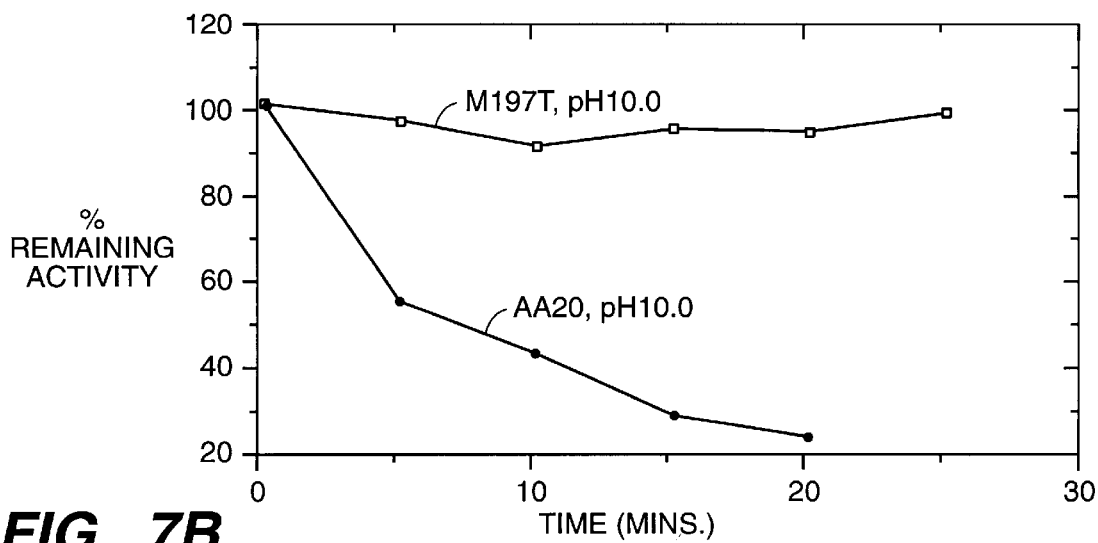
FIG._7B
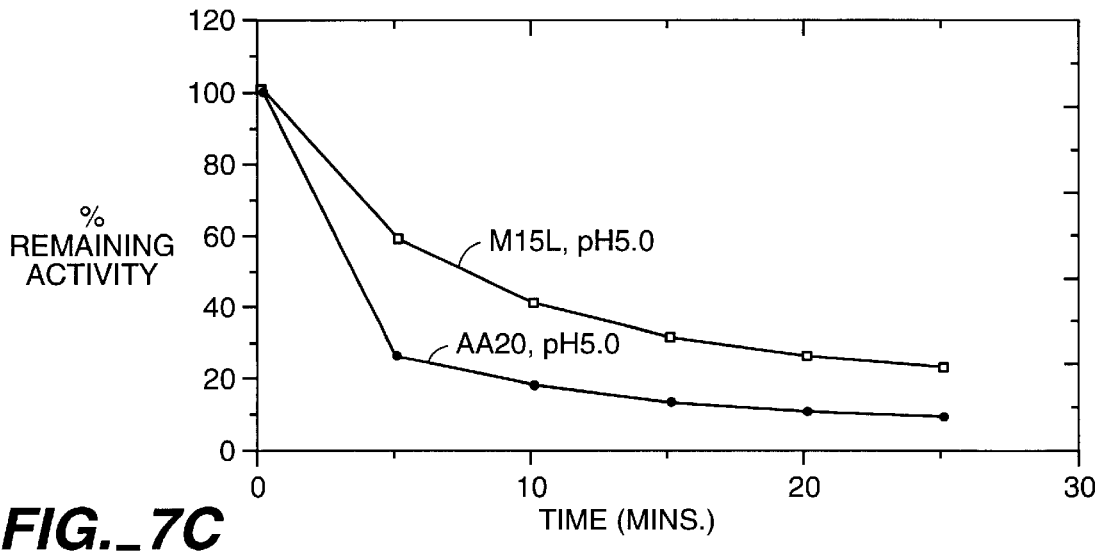
FIG._7C

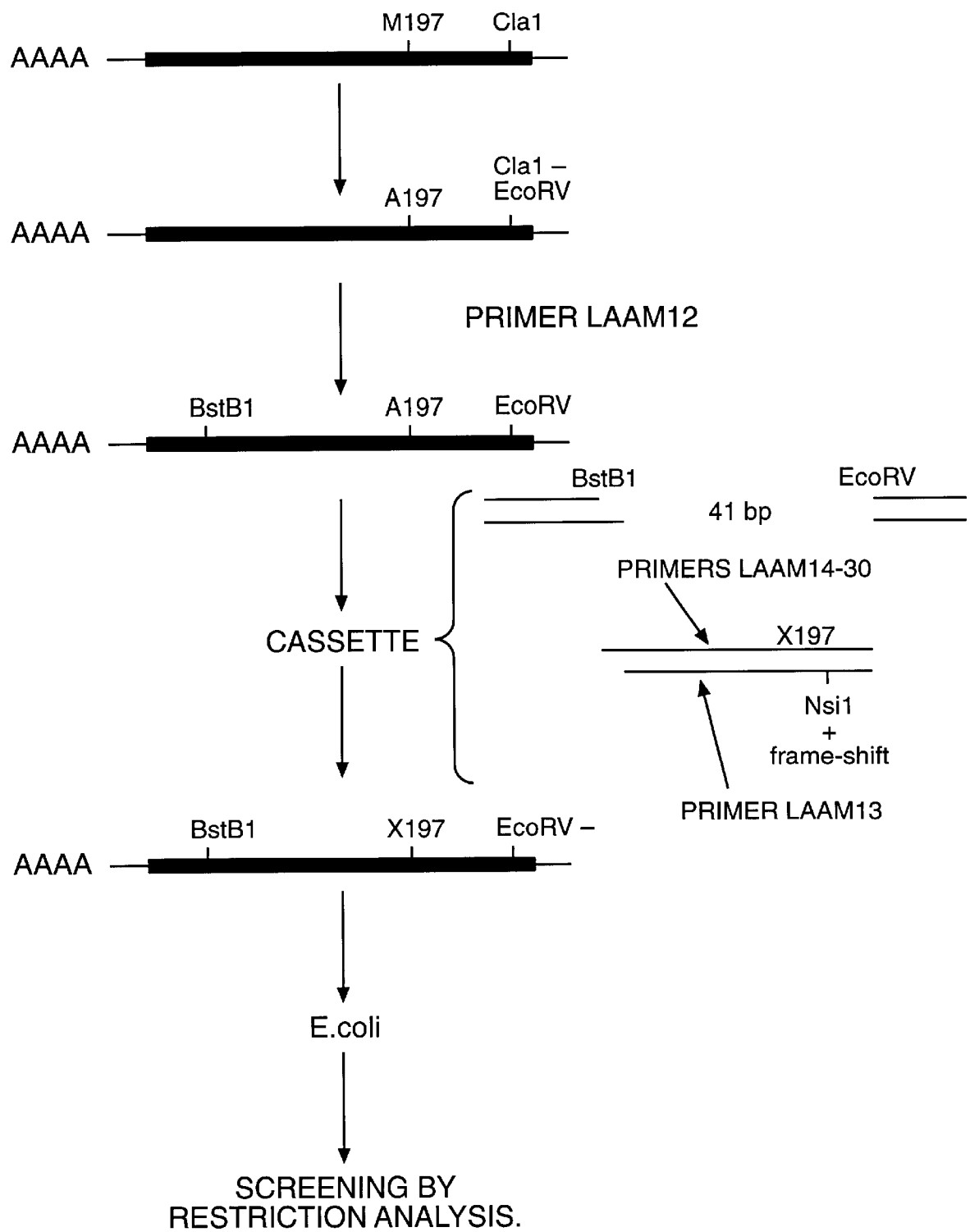
FIG._8

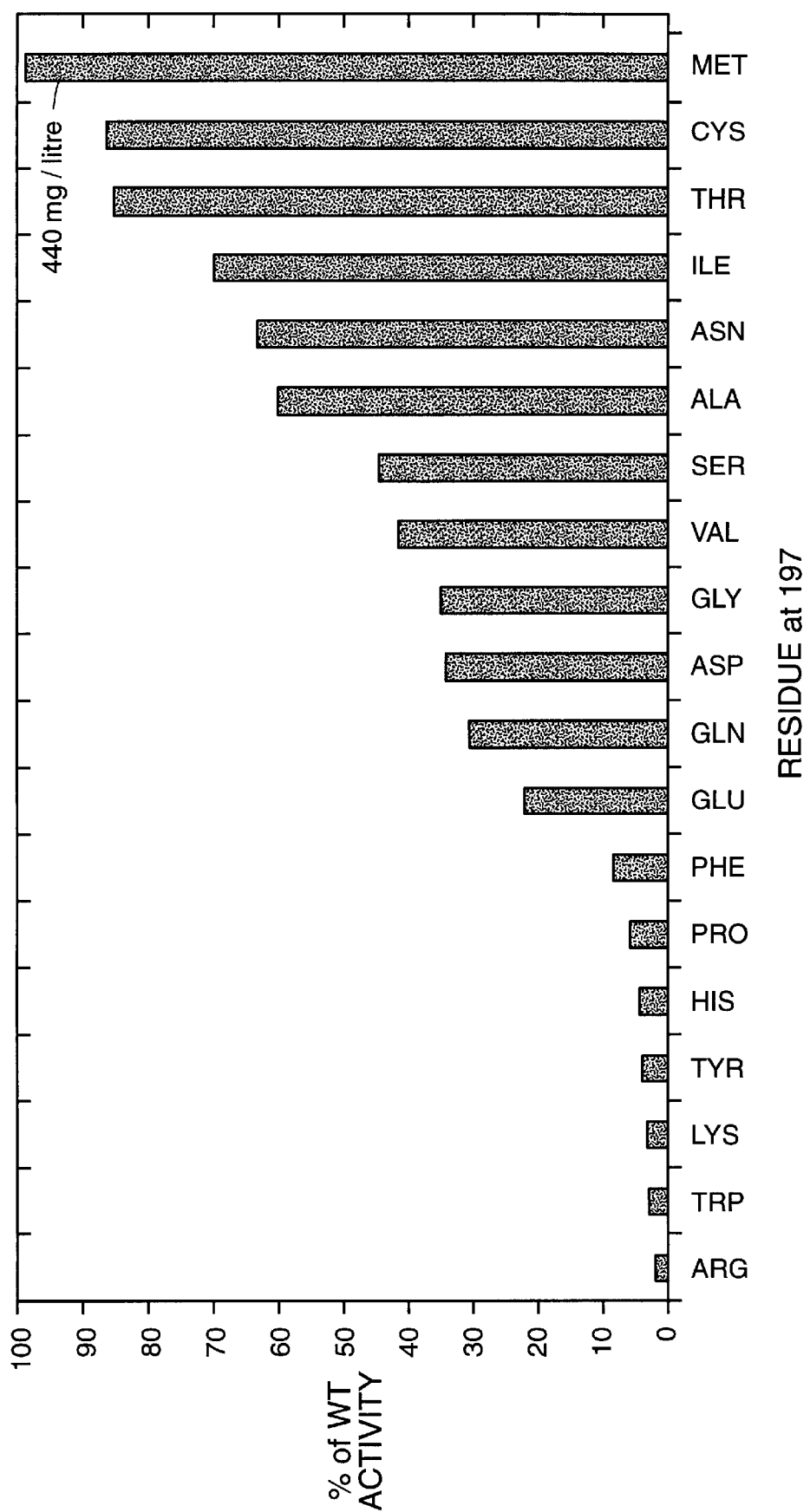
FIG._9

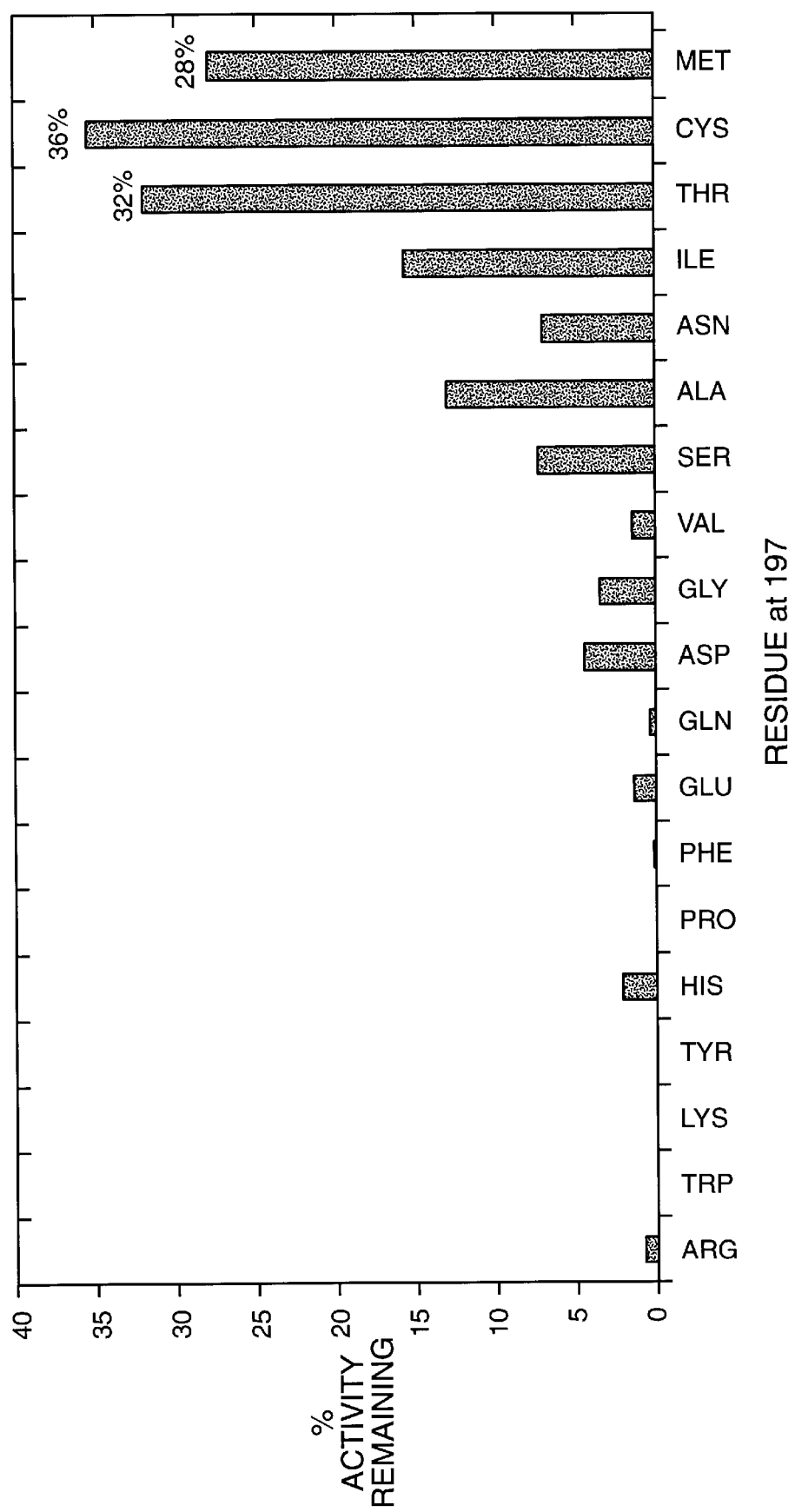
FIG._10

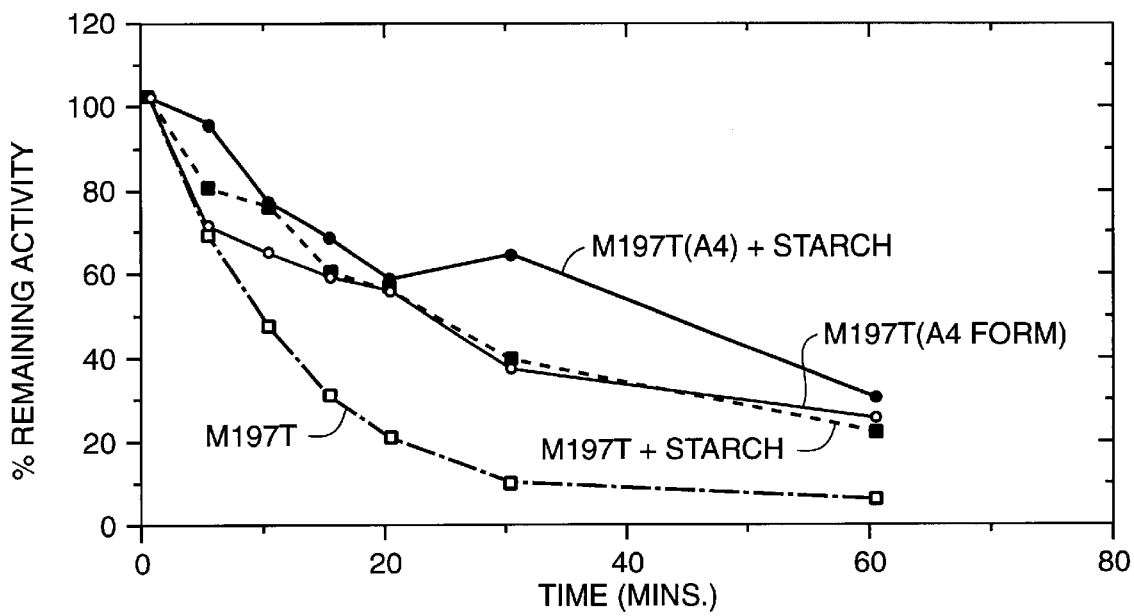
FIG._11A
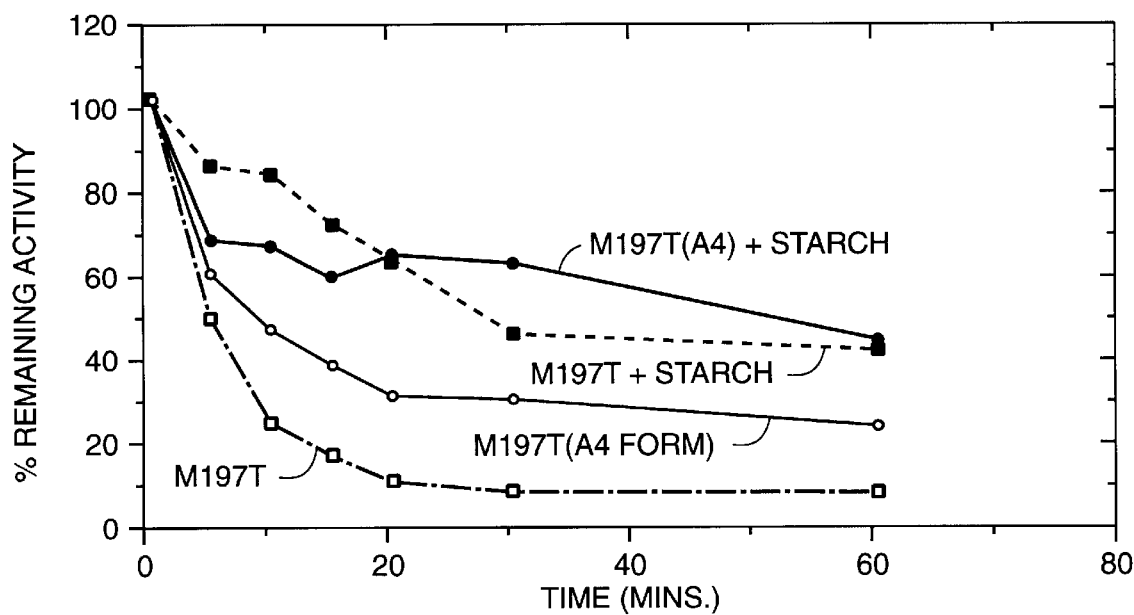
FIG._11B

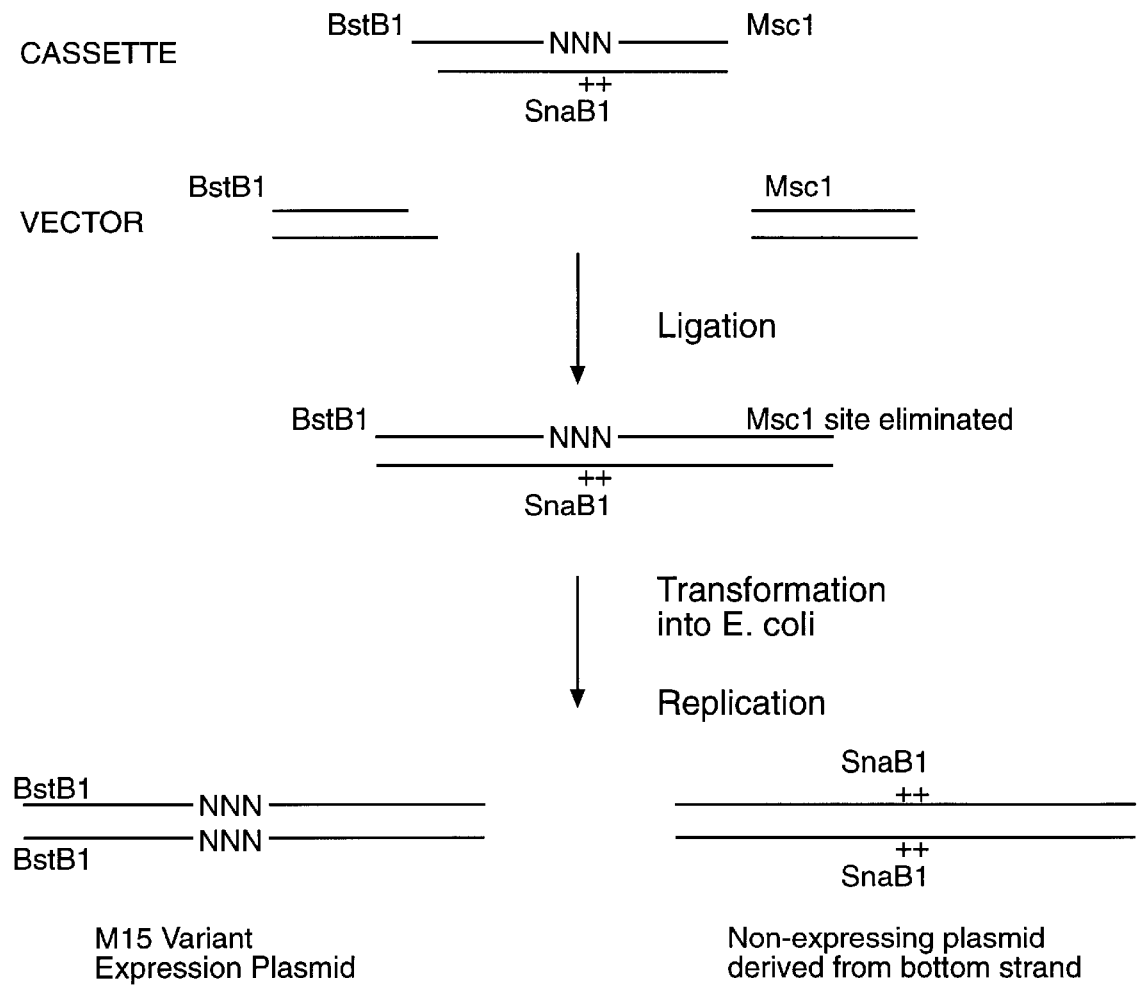
FIG._12

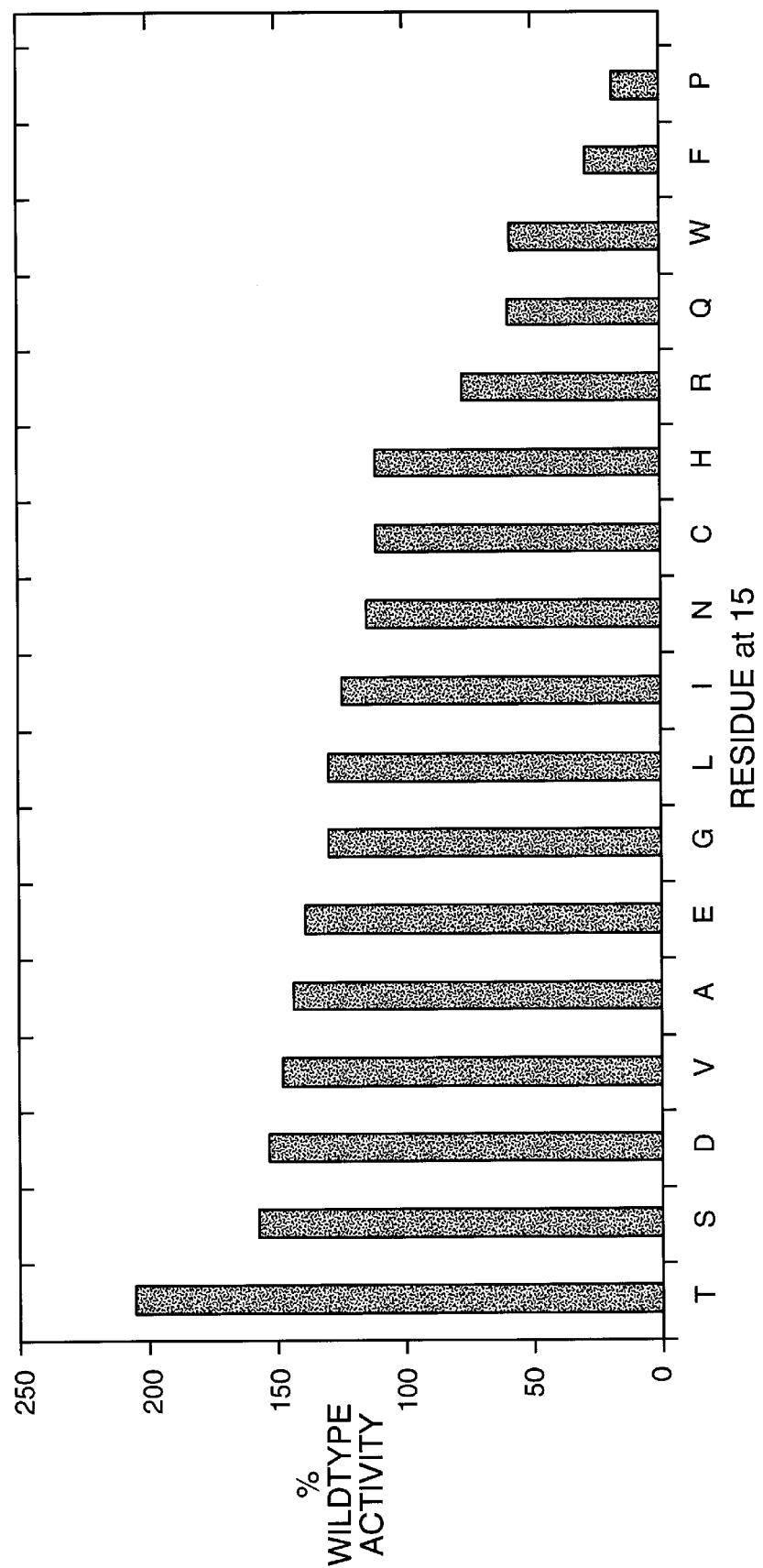
FIG._13

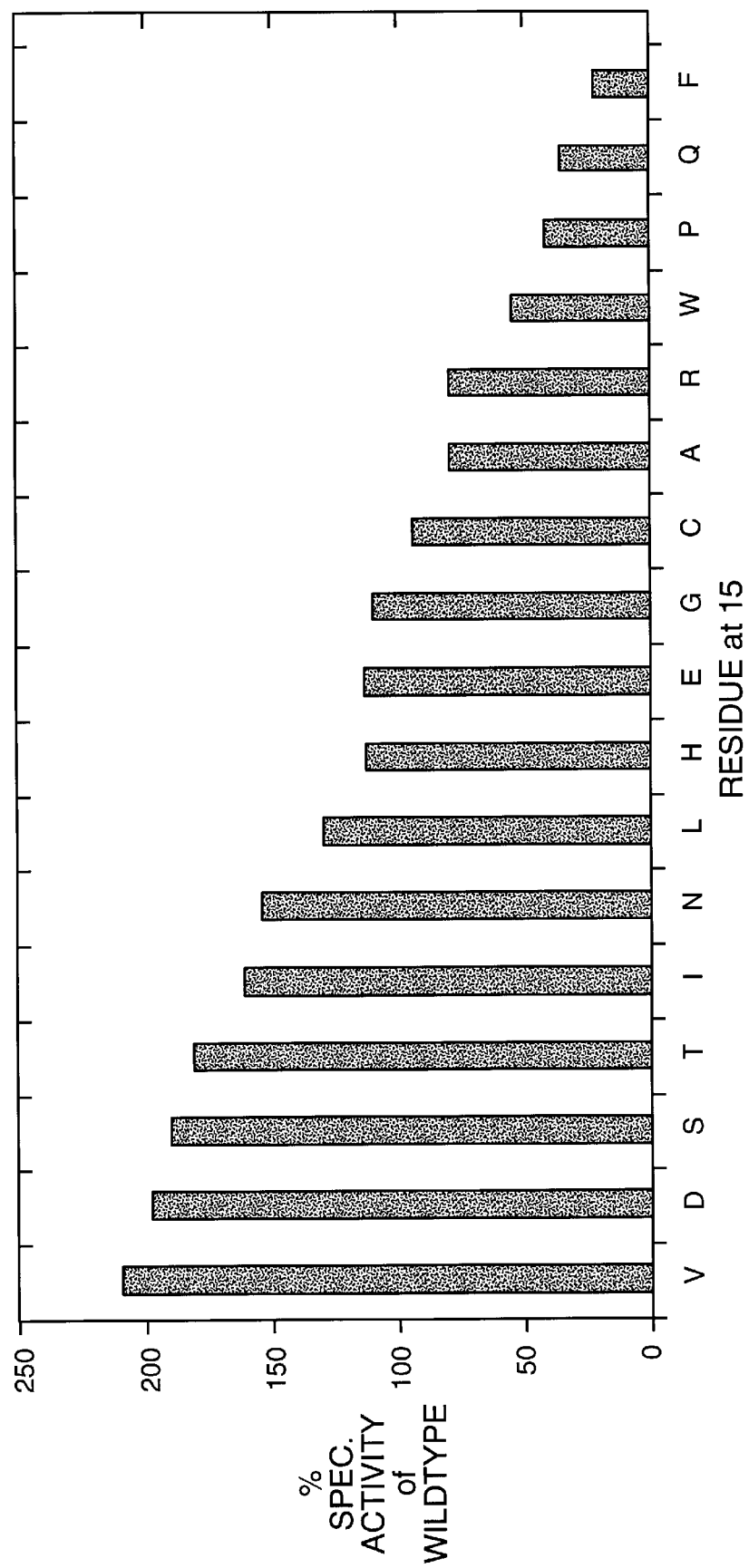
FIG._14

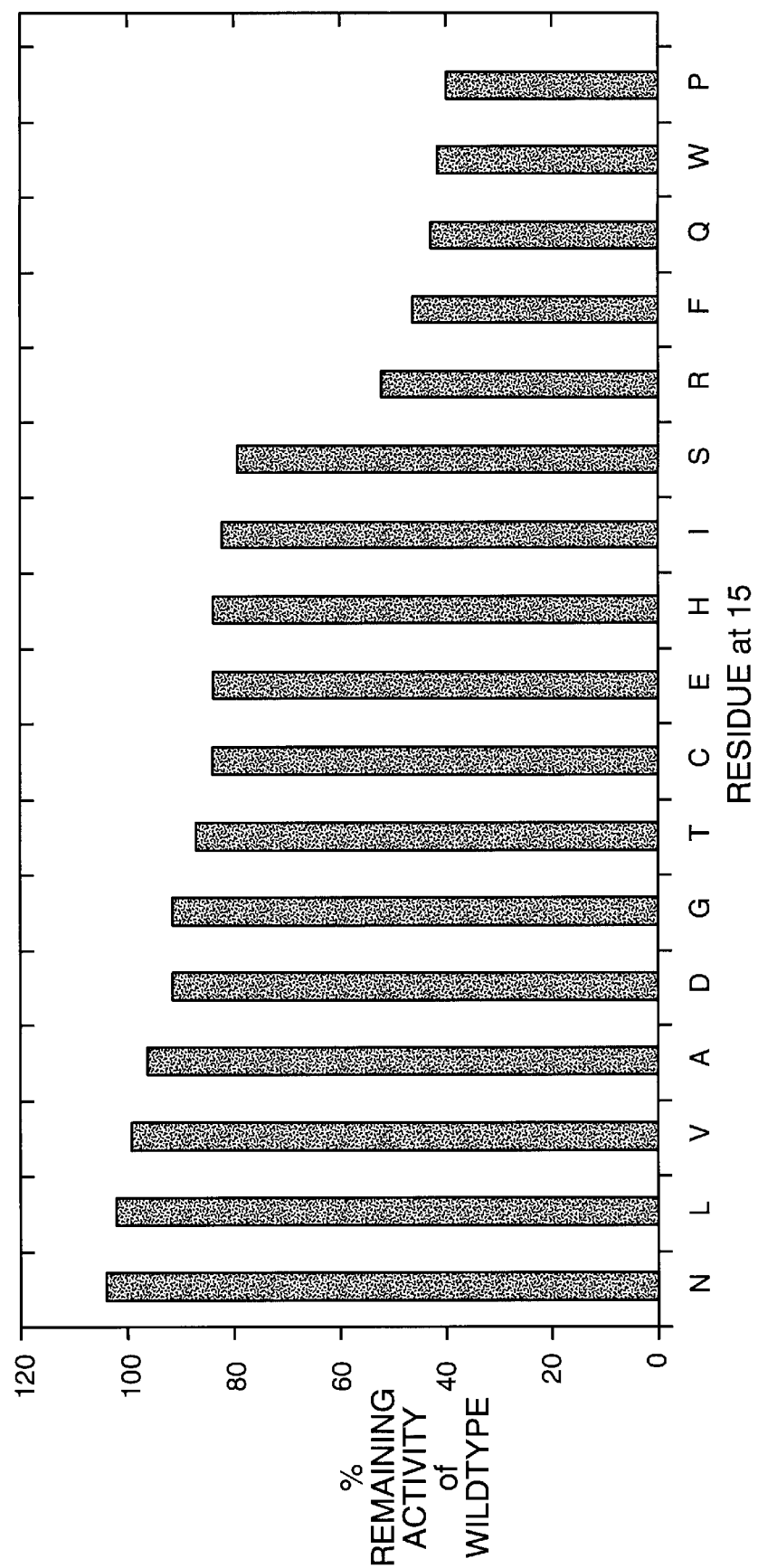
FIG._15

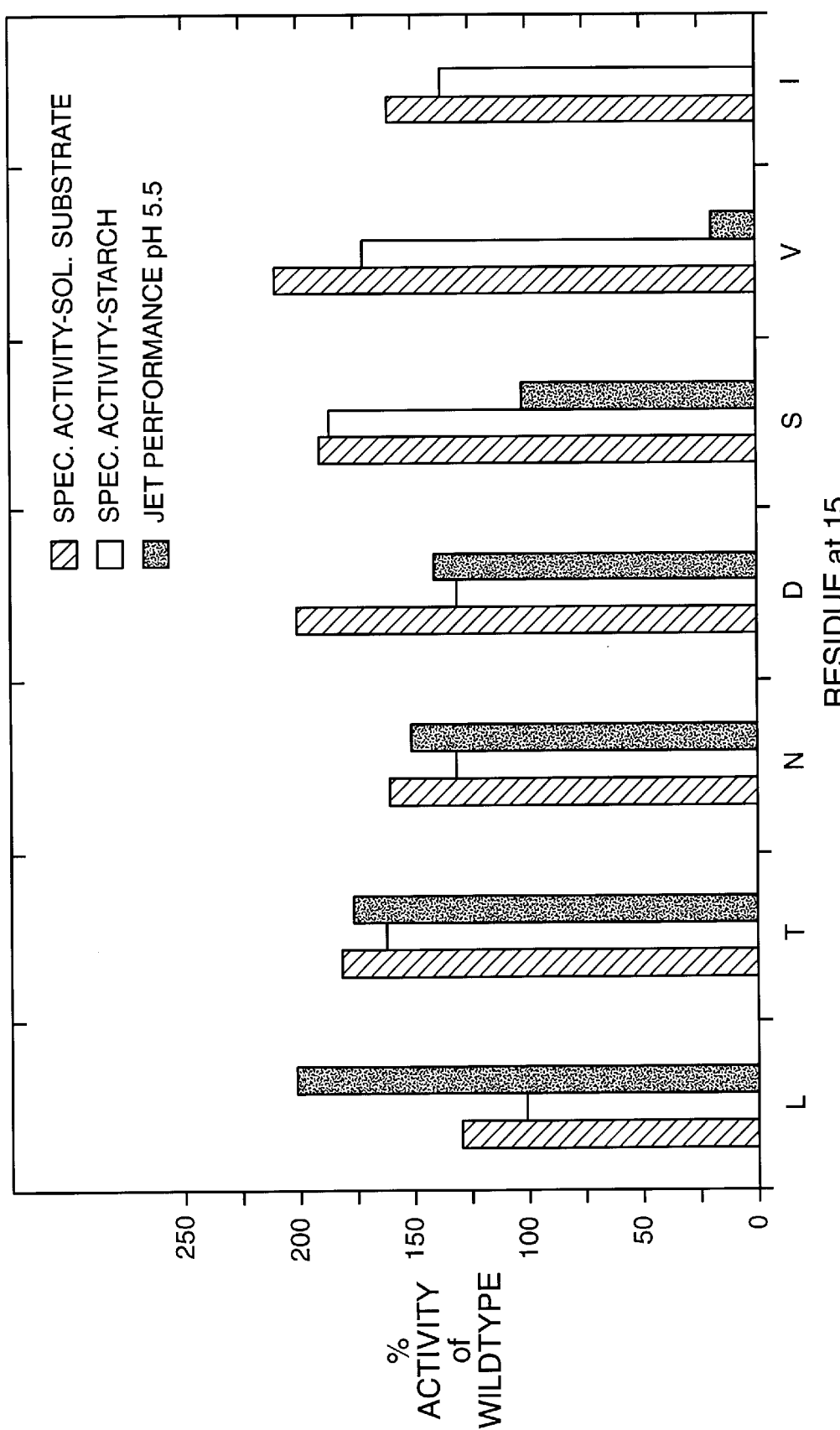
FIG._16

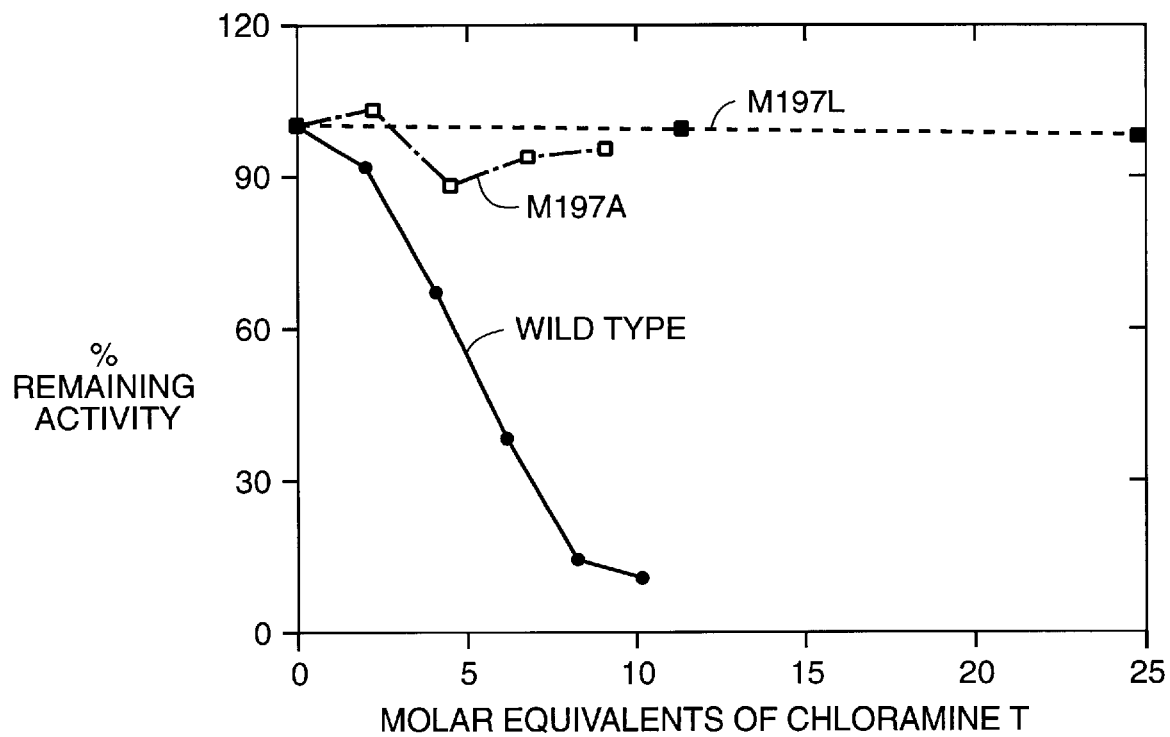
FIG._17
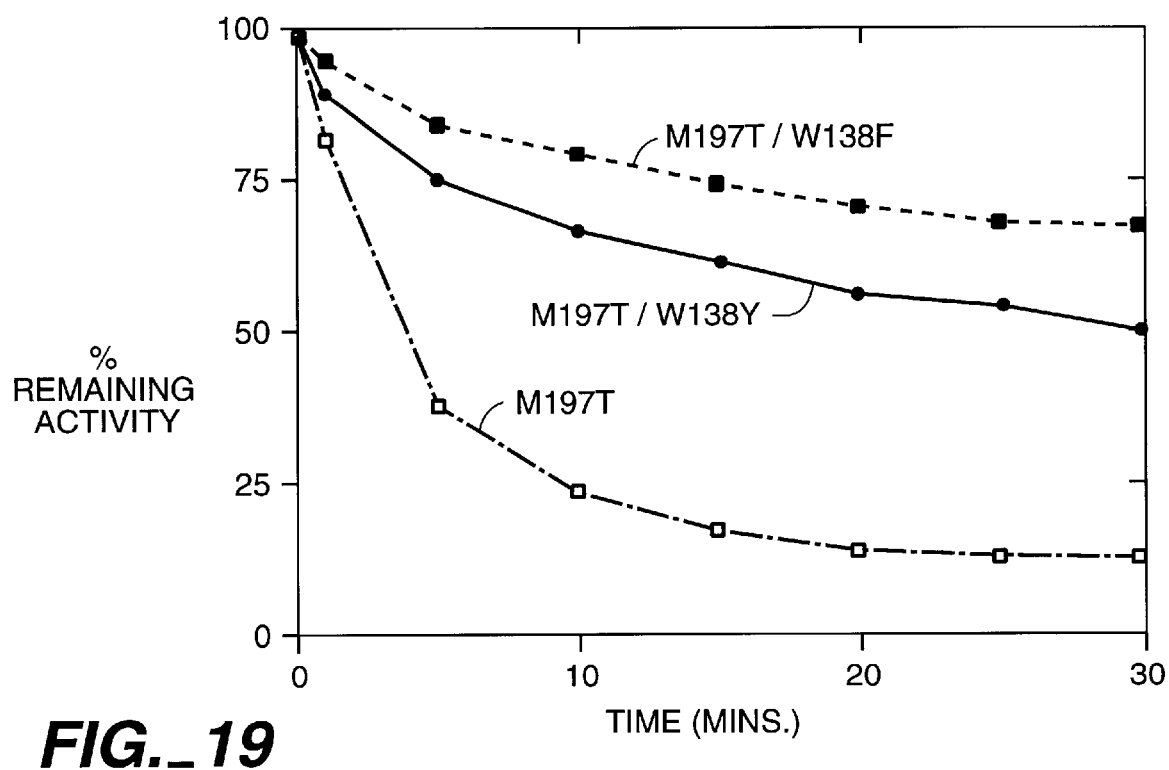
FIG._19

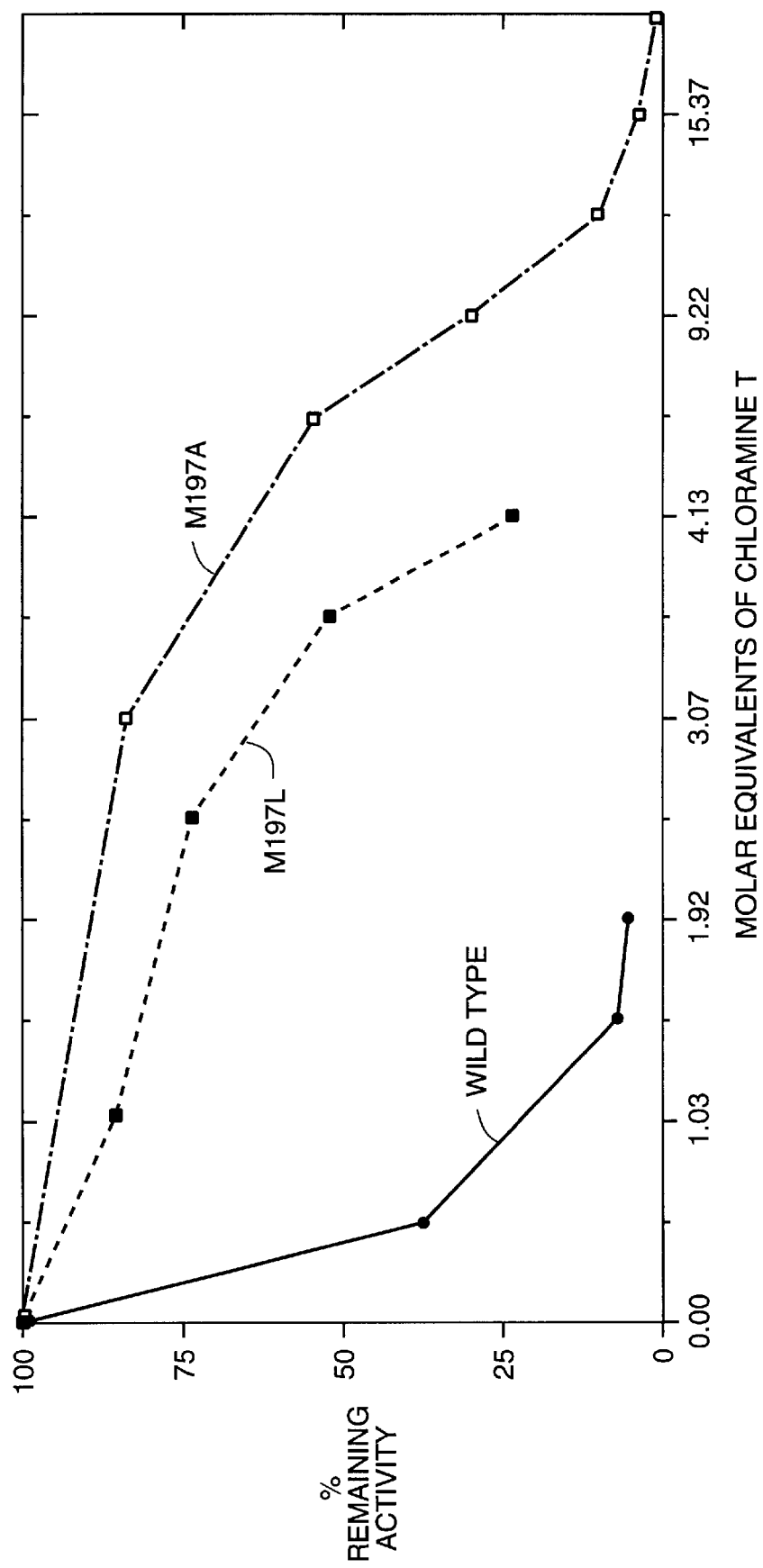
FIG._18

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
      (A) LENGTH: 56 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GATCAAAACA TAAAAAACCG GCCTTGGCCC CGCCGGTTTT TTATTATTTT TGAGCT          56

(2) INFORMATION FOR SEQ ID NO:2:

(i) SEQUENCE CHARACTERISTICS:

```
          (A) LENGTH: 29 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

TGGGACGCTG GCGCAGTACT TTGAATGGT                                    29

(2) INFORMATION FOR SEQ ID NO:3:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

TGATGCAGTA CTTTGAATGG TACCTGCCCA ATGA                              34

(2) INFORMATION FOR SEQ ID NO:4:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:4:

GATTATTTGT TGTATGCCGA TATCGACTAT GACCAT                            36

(2) INFORMATION FOR SEQ ID NO:5:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:5:

CGGGGAAGGA GGCCTTTACG GTAGCT                                       26

(2) INFORMATION FOR SEQ ID NO:6:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:6:

GCGGCTATGA CTTAAGGAAA TTGC                                         24

(2) INFORMATION FOR SEQ ID NO:7:

(i) SEQUENCE CHARACTERISTICS:
          (A) LENGTH: 23 base pairs
          (B) TYPE: nucleic acid
          (C) STRANDEDNESS: single
          (D) TOPOLOGY: linear
```

(ii) MOLECULE TYPE: DNA (genomic)

(xi) SEQUENCE DESCRIPTION: SEQ ID NO:7:

CTACGGGGAT GCATACGGGA CGA                                                    23

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CTACGGGGAT TACTACGGGA CCAAGGGAGA CTCCC                                       35

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCGGTGGGGC CAAGCGGGCC TATGTTGGCC GGCAAA                                      36

(2) INFORMATION FOR SEQ ID NO:10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CATCAGCGTC CCATTAAGAT TTGCAGCCTG CGCAGACATG TTGCT                            45

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GATTATTTGG CGTATGCCGA TATCGACTAT GACCAT                                      36

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGGAAGTTTC GAATGAAAAC G                                           21

(2) INFORMATION FOR SEQ ID NO:13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTCGGCATAT GCATATAATC ATAGTTGCCG TTTTCATT                          38

(2) INFORMATION FOR SEQ ID NO:14:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGAATGAAAA CGGCAACTAT GATTATTTGA TCTATGCCGA C                      41

(2) INFORMATION FOR SEQ ID NO:15:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGAATGAAAA CGGCAACTAT GATTATTTGT TCTATGCCGA C                      41

(2) INFORMATION FOR SEQ ID NO:16:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CGAATGAAAA CGGCAACTAT GATTATTTGG TTTATGCCGA C                      41

(2) INFORMATION FOR SEQ ID NO:17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGAATGAAAA CGGCAACTAT GATTATTTGA GCTATGCCGA C                      41

(2) INFORMATION FOR SEQ ID NO:18:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGAATGAAAA CGGCAACTAT GATTATTTGC CTTATGCCGA C         41

(2) INFORMATION FOR SEQ ID NO:19:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CGAATGAAAA CGGCAACTAT GATTATTTGA CATATGCCGA C         41

(2) INFORMATION FOR SEQ ID NO:20:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

CGAATGAAAA CGGCAACTAT GATTATTTGT ACTATGCCGA C         41

(2) INFORMATION FOR SEQ ID NO:21:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CGAATGAAAA CGGCAACTAT GATTATTTGC ACTATGCCGA C         41

(2) INFORMATION FOR SEQ ID NO:22:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CGAATGAAAA CGGCAACTAT GATTATTTGG GCTATGCCGA C         41

(2) INFORMATION FOR SEQ ID NO:23:

(i) SEQUENCE CHARACTERISTICS:
        (A) LENGTH: 41 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CGAATGAAAA CGGCAACTAT GATTATTTGC AATATGCCGA C                          41

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CGAATGAAAA CGGCAACTAT GATTATTTGA ACTATGCCGA C                          41

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GCAATGAAAA CGGCAACTAT GATTATTTGA AATATGCCGA C                          41

(2) INFORMATION FOR SEQ ID NO:26:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CGAATGAAAA CGGCAACTAT GATTATTTGG ATTATGCCGA C                          41

(2) INFORMATION FOR SEQ ID NO:27:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CGAATGAAAA CGGCAACTAT GATTATTTGG AATATGCCGA C                          41

(2) INFORMATION FOR SEQ ID NO:28:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
CGAATGAAAA CGGCAACTAT GATTATTTGT GTATTGCCGA C                41
```

(2) INFORMATION FOR SEQ ID NO:29:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
CGAATGAAAA CGGCAACTAT GATTATTTGT GGTATGCCGA C                41
```

(2) INFORMATION FOR SEQ ID NO:30:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
CGAATGAAAA CGGCAACTAT GATTATTTGA GATATGCCGA C                41
```

(2) INFORMATION FOR SEQ ID NO:31:

(i) SEQUENCE CHARACTERISTICS:
        (A) LENGTH: 1968 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
AGCTTGAAGA AGTGAAGAAG CAGAGAGGCT ATTGAATAAA TGAGTAGAAA GCGCCATATC      60
GGCGCTTTTC TTTTGGAAGA AAATATAGGG AAAATGGTAC TTGTTAAAAA TTCGGAATAT     120
TTATACAACA TCTATATGTTT CACATTGAAA GGGGAGGAGA ATCATGAAAC AACAAAAACG    180
GCTTTACGCC CGATTGCTGA CGCTGTTATT TGCGCTCATC TTCTTGCTGC CTCATTCTGC    240
AGCAGCGGCG GCAAATCTTA ATGGGACGCT GATGCAGTAT TTTGAATGGT ACATGCCCAA    300
TGACGGCCAA CATTGGAAGC GTTTGCAAAA CGACTCGGCA TATTTGGCTG AACACGGTAT    360
TACTGCCGTC TGGATTCCCC CGGCATATAA GGGAACGAGC CAAGCGGATG TGGGCTACGG    420
TGCTTACGAC CTTTATGATT TAGGGGAGTT TCATCAAAAA GGGACGGTTC GGACAAAGTA    480
CGGCACAAAA GGAGAGCTGC AATCTGCGAT CAAAAGTCTT CATTCCCGCG ACATTAACGT    540
TTACGGGGAT GTGGTCATCA ACCACAAAGG CGGCGCTGAT GCGACCGAAG ATGTAACCGC    600
GGTTGAAGTC GATCCCGCTG ACCGCAACCG CGTAATTTCA GGAGAACACC TAATTAAAGC    660
CTGGACACAT TTTCATTTTC CGGGGCGCGG CAGCACATAC AGCGATTTTA AATGGCATTG    720
GTACCATTTT GACGGAACCG ATTGGGACGA GTCCCGAAAG CTGAACCGCA TCTATAAGTT    780
TCAAGGAAAG GCTTGGGATT GGGAAGTTTC CAATGAAAAC GGCAACTATG ATTATTTGAT    840
GTATGCCGAC ATCGATTATG ACCATCCTGA TGTCGCAGCA GAAATTAAGA GATGGGGCAC    900
```

```
TTGGTATGCC AATGAACTGC AATTGGACGG TTTCCGTCTT GATGCTGTCA AACACATTAA    960

ATTTTCTTTT TTGCGGGATT GGGTTAATCA TGTCAGGGAA AAAACGGGGA AGGAAATGTT   1020

TACGGTAGCT GAATATTGGC AGAATGACTT GGGCGCGCTG GAAAACTATT TGAACAAAAC   1080

AAATTTTAAT CATTCAGTGT TTGACGTGCC GCTTCATTAT CAGTTCCATG CTGCATCGAC   1140

ACAGGGAGGC GGCTATGATA TGAGGAAATT GCTGAACGGT ACGGTCGTTT CCAAGCATCC   1200

GTTGAAATCG GTTACATTTG TCGATAACCA TGATACACAG CCGGGGCAAT CGCTTGAGTC   1260

GACTGTCCAA ACATGGTTTA AGCCGCTTGC TTACGCTTTT ATTCTCACAA GGGAATCTGG   1320

ATACCCTCAG GTTTTCTACG GGGATATGTA CGGGACGAAA GGAGACTCCC AGCGCGAAAT   1380

TCCTGCCTTG AAACACAAAA TTGAACCGAT CTTAAAAGCG AGAAAACAGT ATGCGTACGG   1440

AGCACAGCAT GATTATTTCG ACCACCATGA CATTGTCGGC TGGACAAGGG AAGGCGACAG   1500

CTCGGTTGCA AATTCAGGTT TGGCGGCATT AATAACAGAC GGACCCGGTG GGCAAAGCG   1560

AATGTATGTC GGCCGGCAAA ACGCCGGTGA GACATGGCAT GACATTACCG GAAACCGTTC   1620

GGAGCCGGTT GTCATCAATT CGGAAGGCTG GGGAGAGTTT CACGTAAACG GCGGGTCGGT   1680

TTCAATTTAT GTTCAAAGAT AGAAGAGCAG AGAGGACGGA TTTCCTGAAG GAAATCCGTT   1740

TTTTTATTTT GCCCGTCTTA TAAATTTCTT TGATTACATT TTATAATTAA TTTTAACAAA   1800

GTGTCATCAG CCCTCAGGAA GGACTTGCTG ACAGTTTGAA TCGCATAGGT AAGGCGGGGA   1860

TGAAATGGCA ACGTTATCTG ATGTAGCAAA GAAAGCAAAT GTGTCGAAAA TGACGGTATC   1920

GCGGGTGATC AATCATCCTG AGACTGTGAC GGATGAATTG AAAAAGCT             1968
```

(2) INFORMATION FOR SEQ ID NO:32:

(i) SEQUENCE CHARACTERISTICS:
        (A) LENGTH: 483 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160
```

```
Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
            245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
            290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg (2) INFORMATION FOR SEQ ID NO:33:

(i) SEQUENCE CHARACTERISTICS:
        (A) LENGTH: 511 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn Leu
```

-continued

```
                  20                  25                  30
Asn Gly Thr Leu Met Gln Tyr Phe Glu Trp Tyr Met Pro Asn Asp Gly
            35                  40                  45
His Trp Lys Arg Leu Gln Asn Asp Ser Ala Tyr Leu Ala Glu His Gly
 50                  55                  60
Ile Thr Ala Val Trp Ile Pro Pro Ala Tyr Lys Gly Thr Ser Gln Ala
 65                  70                  75                  80
Asp Val Gly Tyr Gly Ala Tyr Asp Leu Tyr Asp Leu Gly Glu Phe His
                 85                  90                  95
Gln Lys Gly Thr Val Arg Thr Lys Tyr Gly Thr Lys Gly Glu Leu Gln
            100                 105                 110
Ser Ala Ile Lys Ser Leu His Ser Arg Asp Ile Asn Val Tyr Gly Asp
            115                 120                 125
Val Val Ile Asn His Lys Gly Ala Asp Ala Thr Glu Asp Val Thr
130                 135                 140
Ala Val Glu Val Asp Pro Ala Asp Arg Asn Arg Val Ile Ser Gly Glu
145                 150                 155                 160
His Leu Ile Lys Ala Trp Thr His Phe His Phe Pro Gly Arg Gly Ser
                165                 170                 175
Thr Tyr Ser Asp Phe Lys Trp His Trp Tyr His Phe Asp Gly Thr Asp
            180                 185                 190
Trp Asp Glu Ser Arg Lys Leu Asn Arg Ile Tyr Lys Phe Gln Gly Lys
            195                 200                 205
Ala Trp Asp Trp Glu Val Ser Asn Glu Asn Gly Asn Tyr Asp Tyr Leu
            210                 215                 220
Met Tyr Ala Asp Ile Asp Tyr Asp His Pro Asp Val Ala Ala Glu Ile
225                 230                 235                 240
Lys Arg Trp Gly Thr Trp Tyr Ala Asn Glu Leu Gln Leu Asp Gly Phe
                245                 250                 255
Arg Leu Asp Ala Val Lys His Ile Lys Phe Ser Phe Leu Arg Asp Trp
            260                 265                 270
Val Asn His Val Arg Glu Lys Thr Gly Lys Glu Met Phe Thr Val Ala
            275                 280                 285
Glu Tyr Trp Gln Asn Asp Leu Gly Ala Leu Glu Asn Tyr Leu Asn Lys
            290                 295                 300
Thr Asn Phe Asn His Ser Val Phe Asp Val Pro Leu His Tyr Gln Phe
305                 310                 315                 320
His Ala Ala Ser Thr Gln Gly Gly Tyr Asp Met Arg Lys Leu Leu
                325                 330                 335
Asn Gly Thr Val Val Ser Lys His Pro Leu Lys Ser Val Thr Phe Val
            340                 345                 350
Asp Asn His Asp Thr Gln Pro Gly Gln Ser Leu Glu Ser Thr Val Gln
            355                 360                 365
Thr Trp Phe Lys Pro Leu Ala Tyr Ala Phe Ile Leu Thr Arg Glu Ser
            370                 375                 380
Gly Tyr Pro Gln Val Phe Tyr Gly Asp Met Tyr Gly Thr Lys Gly Asp
385                 390                 395                 400
Ser Gln Arg Glu Ile Pro Ala Leu Lys His Lys Ile Glu Pro Ile Leu
                405                 410                 415
Lys Ala Arg Lys Gln Tyr Ala Tyr Gly Ala Gln His Asp Tyr Phe Asp
            420                 425                 430
His His Asp Ile Val Gly Trp Thr Arg Glu Gly Asp Ser Ser Val Ala
            435                 440                 445
```

```
Asn Ser Gly Leu Ala Ala Leu Ile Thr Asp Pro Gly Gly Ala Lys
    450                 455                 460

Arg Met Tyr Val Gly Arg Gln Asn Ala Gly Glu Thr Trp His Asp Ile
465                 470                 475                 480

Thr Gly Asn Arg Ser Glu Pro Val Val Ile Asn Ser Glu Gly Trp Gly
                485                 490                 495

Glu Phe His Val Asn Gly Gly Ser Val Ser Ile Tyr Val Gln Arg
                500                 505                 510

(2) INFORMATION FOR SEQ ID NO:34:

(i) SEQUENCE CHARACTERISTICS:
        (A) LENGTH: 520 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Met Arg Gly Arg Gly Asn Met Ile Gln Lys Arg Lys Arg Thr Val Ser
1               5                   10                  15

Phe Arg Leu Val Leu Met Cys Thr Leu Leu Phe Val Ser Leu Pro Ile
                20                  25                  30

Thr Lys Thr Ser Ala Val Asn Gly Thr Leu Met Gln Tyr Phe Glu Trp
            35                  40                  45

Tyr Thr Pro Asn Asp Gly Gln His Trp Lys Arg Leu Gln Asn Asp Ala
        50                  55                  60

Glu His Leu Ser Asp Ile Gly Ile Thr Ala Val Trp Ile Pro Pro Ala
65                  70                  75                  80

Tyr Lys Gly Leu Ser Gln Ser Asp Asn Gly Tyr Gly Pro Tyr Asp Leu
                85                  90                  95

Tyr Asp Leu Gly Glu Phe Gln Gln Lys Gly Thr Val Arg Thr Lys Tyr
                100                 105                 110

Gly Thr Lys Ser Glu Leu Gln Asp Ala Ile Gly Ser Leu His Ser Arg
                115                 120                 125

Asn Val Gln Val Tyr Gly Asp Val Val Leu Asn His Lys Ala Gly Ala
    130                 135                 140

Asp Ala Thr Glu Asp Val Thr Ala Val Glu Val Asn Pro Ala Asn Arg
145                 150                 155                 160

Asn Gln Glu Thr Ser Glu Glu Tyr Gln Ile Lys Ala Trp Thr Asp Phe
                165                 170                 175

Arg Phe Pro Gly Arg Gly Asn Thr Tyr Ser Asp Phe Lys Trp His Trp
                180                 185                 190

Tyr His Phe Asp Gly Ala Asp Trp Asp Glu Ser Arg Lys Ile Ser Arg
                195                 200                 205

Ile Phe Lys Phe Arg Gly Glu Gly Lys Ala Trp Asp Trp Glu Val Ser
    210                 215                 220

Ser Glu Asn Gly Asn Tyr Asp Tyr Leu Met Tyr Ala Asp Val Asp Tyr
225                 230                 235                 240

Asp His Pro Asp Val Val Ala Glu Thr Lys Lys Trp Gly Ile Trp Tyr
                245                 250                 255

Ala Asn Glu Leu Ser Leu Asp Gly Phe Arg Ile Asp Ala Ala Lys His
                260                 265                 270

Ile Lys Phe Ser Phe Leu Arg Asp Trp Val Gln Ala Val Arg Gln Ala
    275                 280                 285
```

```
Thr Gly Lys Glu Met Phe Thr Val Ala Glu Tyr Trp Gln Asn Asn Ala
    290                 295                 300

Gly Lys Leu Glu Asn Tyr Leu Asn Lys Thr Ser Phe Asn Gln Ser Val
305                 310                 315                 320

Phe Asp Val Pro Leu His Phe Asn Leu Gln Ala Ala Ser Ser Gln Gly
                325                 330                 335

Gly Gly Tyr Asp Met Arg Arg Leu Leu Asp Gly Thr Val Val Ser Arg
            340                 345                 350

His Pro Glu Lys Ala Val Thr Phe Val Glu Asn His Asp Thr Gln Pro
        355                 360                 365

Gly Gln Ser Leu Glu Ser Thr Val Gln Thr Trp Phe Lys Pro Leu Ala
    370                 375                 380

Tyr Ala Phe Ile Leu Thr Arg Glu Ser Gly Tyr Pro Gln Val Phe Tyr
385                 390                 395                 400

Gly Asp Met Tyr Gly Thr Lys Gly Thr Ser Pro Lys Glu Ile Pro Ser
                405                 410                 415

Leu Lys Asp Asn Ile Glu Pro Ile Leu Lys Ala Arg Lys Glu Tyr Ala
            420                 425                 430

Tyr Gly Pro Gln His Asp Tyr Ile Asp His Pro Asp Val Ile Gly Trp
        435                 440                 445

Thr Arg Glu Gly Asp Ser Ser Ala Ala Lys Ser Gly Leu Ala Ala Leu
    450                 455                 460

Ile Thr Asp Gly Pro Gly Gly Ser Lys Arg Met Tyr Ala Gly Leu Lys
465                 470                 475                 480

Asn Ala Gly Glu Thr Trp Tyr Asp Ile Thr Gly Asn Arg Ser Asp Thr
                485                 490                 495

Val Lys Ile Gly Ser Asp Gly Trp Gly Glu Phe His Val Asn Asp Gly
            500                 505                 510

Ser Val Ser Ile Tyr Val Gln Lys
        515                 520

(2) INFORMATION FOR SEQ ID NO:35:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Val Leu Thr Phe His Arg Ile Ile Arg Lys Gly Trp Met Phe Leu Leu
1               5                   10                  15

Ala Phe Leu Leu Thr Ala Ser Leu Phe Cys Pro Thr Gly Arg His Ala
            20                  25                  30

Lys Ala Ala Ala Pro Phe Asn Gly Thr Met Met Gln Tyr Phe Glu Trp
        35                  40                  45

Tyr Leu Pro Asp Asp Gly Thr Leu Trp Thr Lys Val Ala Asn Glu Ala
    50                  55                  60

Asn Asn Leu Ser Ser Leu Gly Ile Thr Ala Leu Ser Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110
```

-continued

```
Gly Thr Lys Ala Gln Tyr Leu Gln Ala Ile Gln Ala Ala His Ala Ala
        115                 120                 125
Gly Met Gln Val Tyr Ala Asp Val Val Phe Asp His Lys Gly Gly Ala
    130                 135                 140
Asp Gly Thr Glu Trp Val Asp Ala Val Glu Val Asn Pro Ser Asp Arg
145                 150                 155                 160
Asn Gln Glu Ile Ser Gly Thr Tyr Gln Ile Gln Ala Trp Thr Lys Phe
                165                 170                 175
Asp Phe Pro Gly Arg Gly Asn Thr Tyr Ser Ser Phe Lys Trp Arg Trp
            180                 185                 190
Tyr His Phe Asp Gly Val Asp Trp Asp Glu Ser Arg Lys Leu Ser Arg
        195                 200                 205
Ile Tyr Lys Phe Arg Gly Ile Gly Lys Ala Trp Asp Trp Glu Val Asp
    210                 215                 220
Thr Glu Asn Gly Asn Tyr Asp Tyr Leu Met Tyr Ala Asp Leu Asp Met
225                 230                 235                 240
Asp His Pro Glu Val Val Thr Glu Leu Lys Asn Trp Gly Lys Trp Tyr
                245                 250                 255
Val Asn Thr Thr Asn Ile Asp Gly Phe Arg Leu Asp Gly Leu Lys His
            260                 265                 270
Ile Lys Phe Ser Phe Phe Pro Asp Trp Leu Ser Tyr Val Arg Ser Gln
        275                 280                 285
Thr Gly Lys Pro Leu Phe Thr Val Gly Glu Tyr Trp Ser Tyr Asp Ile
    290                 295                 300
Asn Lys Leu His Asn Tyr Ile Thr Lys Thr Asn Gly Thr Met Ser Leu
305                 310                 315                 320
Phe Asp Ala Pro Leu His Asn Lys Phe Tyr Thr Ala Ser Lys Ser Gly
                325                 330                 335
Gly Ala Phe Asp Met Arg Thr Leu Met Thr Asn Thr Leu Met Lys Asp
            340                 345                 350
Gln Pro Thr Leu Ala Val Thr Phe Val Asp Asn His Asp Thr Asn Pro
        355                 360                 365
Ala Lys Arg Cys Ser His Gly Arg Pro Trp Phe Lys Pro Leu Ala Tyr
    370                 375                 380
Ala Phe Ile Leu Thr Arg Gln Glu Gly Tyr Pro Cys Val Phe Tyr Gly
385                 390                 395                 400
Asp Tyr Tyr Gly Ile Pro Gln Tyr Asn Ile Pro Ser Leu Lys Ser Lys
                405                 410                 415
Ile Asp Pro Leu Leu Ile Ala Arg Arg Asp Tyr Ala Tyr Gly Thr Gln
            420                 425                 430
His Asp Tyr Leu Asp His Ser Asp Ile Ile Gly Trp Thr Arg Glu Gly
        435                 440                 445
Val Thr Glu Lys Pro Gly Ser Gly Leu Ala Ala Leu Ile Thr Asp Gly
    450                 455                 460
Ala Gly Arg Ser Lys Trp Met Tyr Val Gly Lys Gln His Ala Gly Lys
465                 470                 475                 480
Val Phe Tyr Asp Leu Thr Gly Asn Arg Ser Asp Thr Val Thr Ile Asn
                485                 490                 495
Ser Asp Gly Trp Gly Glu Phe Lys Val Asn Gly Gly Ser Val Ser Val
            500                 505                 510
Trp Val Pro Arg Lys Thr Thr Val Ser Thr Ile Ala Arg Pro Ile Thr
        515                 520                 525
```

```
Thr Arg Pro Trp Thr Gly Glu Phe Val Arg Trp His Glu Pro Arg Leu
    530                 535                 540

Val Ala Trp Pro
545
```

(2) INFORMATION FOR SEQ ID NO:36:

(i) SEQUENCE CHARACTERISTICS:
        (A) LENGTH: 483 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Thr Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320
```

```
Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
                370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
                450                 455                 460

Glu Gly Trp Gly Glu Phe His Val Asn Gly Gly Ser Val Ser Ile Tyr
465                 470                 475                 480

Val Gln Arg
```

(2) INFORMATION FOR SEQ ID NO:37:

(i) SEQUENCE CHARACTERISTICS:
        (A) LENGTH: 487 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Ala Ala Ala Ala Ala Asn Leu Asn Gly Thr Leu Met Gln Tyr Phe Glu
1               5                   10                  15

Trp Tyr Met Pro Asn Asp Gly Gln His Trp Lys Arg Leu Gln Asn Asp
                20                  25                  30

Ser Ala Tyr Leu Ala Glu His Gly Ile Thr Ala Val Trp Ile Pro Pro
                35                  40                  45

Ala Tyr Lys Gly Thr Ser Gln Ala Asp Val Gly Tyr Gly Ala Tyr Asp
50                  55                  60

Leu Tyr Asp Leu Gly Glu Phe His Gln Lys Gly Thr Val Arg Thr Lys
65                  70                  75                  80

Tyr Gly Thr Lys Gly Glu Leu Gln Ser Ala Ile Lys Ser Leu His Ser
                85                  90                  95

Arg Asp Ile Asn Val Tyr Gly Asp Val Val Ile Asn His Lys Gly Gly
                100                 105                 110

Ala Asp Ala Thr Glu Asp Val Thr Ala Val Glu Val Asp Pro Ala Asp
                115                 120                 125

Arg Asn Arg Val Ile Ser Gly Glu His Leu Ile Lys Ala Trp Thr His
                130                 135                 140

Phe His Phe Pro Gly Arg Gly Ser Thr Tyr Ser Asp Phe Lys Trp His
145                 150                 155                 160

Trp Tyr His Phe Asp Gly Thr Asp Trp Asp Glu Ser Arg Lys Leu Asn
                165                 170                 175

Arg Ile Tyr Lys Phe Gln Gly Lys Ala Trp Asp Trp Glu Val Ser Asn
```

-continued

```
                  180                 185                 190
Glu Asn Gly Asn Tyr Asp Tyr Leu Met Tyr Ala Asp Ile Asp Tyr Asp
            195                 200                 205

His Pro Asp Val Ala Ala Glu Ile Lys Arg Trp Gly Thr Trp Tyr Ala
        210                 215                 220

Asn Glu Leu Gln Leu Asp Gly Phe Arg Leu Asp Ala Val Lys His Ile
225                 230                 235                 240

Lys Phe Ser Phe Leu Arg Asp Trp Val Asn His Val Arg Glu Lys Thr
                245                 250                 255

Gly Lys Glu Met Phe Thr Val Ala Glu Tyr Trp Gln Asn Asp Leu Gly
            260                 265                 270

Ala Leu Glu Asn Tyr Leu Asn Lys Thr Asn Phe Asn His Ser Val Phe
        275                 280                 285

Asp Val Pro Leu His Tyr Gln Phe His Ala Ala Ser Thr Gln Gly Gly
        290                 295                 300

Gly Tyr Asp Met Arg Lys Leu Leu Asn Gly Thr Val Val Ser Lys His
305                 310                 315                 320

Pro Leu Lys Ser Val Thr Phe Val Asp Asn His Asp Thr Gln Pro Gly
                325                 330                 335

Gln Ser Leu Glu Ser Thr Val Gln Thr Trp Phe Lys Pro Leu Ala Tyr
            340                 345                 350

Ala Phe Ile Leu Thr Arg Glu Ser Gly Tyr Pro Gln Val Phe Tyr Gly
        355                 360                 365

Asp Met Tyr Gly Thr Lys Gly Asp Ser Gln Arg Glu Ile Pro Ala Leu
        370                 375                 380

Lys His Lys Ile Glu Pro Ile Leu Lys Ala Arg Lys Gln Tyr Ala Tyr
385                 390                 395                 400

Gly Ala Gln His Asp Tyr Phe Asp His His Asp Ile Val Gly Trp Thr
                405                 410                 415

Arg Glu Gly Asp Ser Ser Val Ala Asn Ser Gly Leu Ala Ala Leu Ile
            420                 425                 430

Thr Asp Gly Pro Gly Gly Ala Lys Arg Met Tyr Val Gly Arg Gln Asn
        435                 440                 445

Ala Gly Glu Thr Trp His Asp Ile Thr Gly Asn Arg Ser Glu Pro Val
        450                 455                 460

Val Ile Asn Ser Glu Gly Trp Gly Glu Phe His Val Asn Gly Gly Ser
465                 470                 475                 480

Val Ser Ile Tyr Val Gln Arg
                485
```

(2) INFORMATION FOR SEQ ID NO:38:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Met Lys Gln Gln Lys Arg Leu Thr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30
```

(2) INFORMATION FOR SEQ ID NO:39:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

```
Met Arg Ser Lys Thr Leu Trp Ile Ser Leu Leu Phe Ala Leu Thr Leu
1               5                  10                  15

Ile Phe Thr Met Ala Phe Ser Asn Met Ser Ala Gln Ala Ala Gly Lys
            20                  25                  30

Ser
```

(2) INFORMATION FOR SEQ ID NO:40:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

```
Met Arg Ser Lys Thr Leu Trp Ile Ser Leu Leu Phe Ala Leu Thr Leu
1               5                  10                  15

Ile Phe Thr Met Ala Phe Ser Asn Met Ser Ala Gln Ala Ala Ala Ala
            20                  25                  30

Ala Ala Asn
        35
```

(2) INFORMATION FOR SEQ ID NO:41:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
Met Arg Ser Lys Thr Leu Trp Ile Ser Leu Leu Phe Ala Leu Thr Leu
1               5                  10                  15

Ile Phe Thr Met Ala Phe Ser Asn Met Ser Ala Gln Ala Ala Asn Leu
            20                  25                  30
```

(2) INFORMATION FOR SEQ ID NO:42:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

CACCTAATTA AAGCTTTCAC ACATTTTCAT TTT                    33

(2) INFORMATION FOR SEQ ID NO:43:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

CACCTAATTA AAGCTTACAC ACATTTTCAT TTT                                      33

(2) INFORMATION FOR SEQ ID NO:44:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

CCGCGTAATT TCCGGAGAAC ACCTAATTAA AGCCGCAACA CATTTTCATT TTCCCGGGCG         60

CGGCAG                                                                    66

(2) INFORMATION FOR SEQ ID NO:45:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

CCGGAGAACA CCTAATTAAA GCCCTAACAC ATTTTCATTT TC                            42

(2) INFORMATION FOR SEQ ID NO:46:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

CCGGAGAACA CCTAATTAAA GCCCACACAC ATTTTCATTT TC                            42

(2) INFORMATION FOR SEQ ID NO:47:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

CCGGAGAACA CCTAATTAAA GCCTGCACAC ATTTTCATTT TC                            42

(2) INFORMATION FOR SEQ ID NO:48:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

GATGCAGTAT TTCGAACTGG TATA                                              24

(2) INFORMATION FOR SEQ ID NO:49:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

TGCCCAATGA TGGCCAACAT TGGAAG                                            26

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

CGAATGGTAT GCTCCCAATG ACGG                                              24

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

CGAATGGTAT CGCCCCAATG ACGG                                              24

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

CGAATGGTAT AATCCCAATG ACGG                                              24

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

CGAATGGTAT GATCCCAATG ACGG                                         24

(2) INFORMATION FOR SEQ ID NO:54:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

CGAATGGTAT CACCCCAATG ACGG                                         24

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

CGAATGGTAT AAACCCAATG ACGG                                         24

(2) INFORMATION FOR SEQ ID NO:56:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

CGAATGGTAT CCGCCCAATG ACGG                                         24

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

CGAATGGTAT TCTCCCAATG ACGG                                         24

(2) INFORMATION FOR SEQ ID NO:58:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

```
CGAATGGTAC ACTCCCAATG ACGG                                              24
```

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

```
CGAATGGTAT GTTCCCAATG ACGG                                              24
```

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
CGAATGGTAT TGTCCCAATG ACGG                                              24
```

(2) INFORMATION FOR SEQ ID NO:61:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
CGAATGGTAT CAACCCAATG ACGG                                              24
```

(2) INFORMATION FOR SEQ ID NO:62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

```
CGAATGGTAT GAACCCAATG ACGG                                              24
```

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

```
CGAATGGTAT GGTCCCAATG ACGG                                              24
```

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

CGAATGGTAT ATTCCCAATG ACGG                                              24

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

CGAATGGTAT TTTCCCAATG ACGG                                              24

(2) INFORMATION FOR SEQ ID NO:66:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

CGAATGGTAC TGGCCCAATG ACGG                                              24

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

CGAATGGTAT TATCCCAATG ACGG                                              24

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

CCGTCATTGG GACTACGTAC CATT                                              24

OXIDATIVELY STABLE ALPHA-AMYLASE

RELATED APPLICATIONS

This application is a continuation-in-part of U.S. Ser. No. 08/016,395 filed Feb. 11, 1993, now abandoned.

FIELD OF THE INVENTION

The present invention relates to novel alpha-amylase mutants having an amino acid sequence not found in nature, such mutants having an amino acid sequence wherein one or more amino acid residue(s) of a precursor alpha-amylase, specifically any oxidizable amino acid, have been substituted with a different amino acid. The mutant enzymes of the present invention exhibit altered stability/activity profiles including but not limited to altered oxidative stability, altered pH performance profile, altered specific activity and/or altered thermostability.

BACKGROUND OF THE INVENTION

Alpha-amylases (alpha-1,4-glucan-4-glucanohydrolase, EC3.2.1.1) hydrolyze internal alpha-1,4-glucosidic linkages in starch largely at random, to produce smaller molecular weight malto-dextrins. Alpha-amylases are of considerable commercial value, being used in the initial stages (liquefaction) of starch processing; in alcohol production; as cleaning agents in detergent matrices; and in the textile industry for starch desizing. Alpha-amylases are produced by a wide variety of microorganisms including Bacillus and Aspergillus, with most commercial amylases being produced from bacterial sources such as *B. licheniformis, B. amyloliquefaciens, B. subtilis,* or *B. stearothermophilus*. In recent years the preferred enzymes in commercial use have been those from *B. licheniformis* because of their heat stability and performance, at least at neutral and mildly alkaline pH's.

Previously there have been studies using recombinant DNA techniques to explore which residues are important for the catalytic activity of amylases and/or to explore the effect of modifying certain amino acids within the active site of various amylases (Vihinen, M. et al. (1990) J. Bichem. 107:267–272; Holm, L. et al. (1990) Protein Engineering 3:181–191; Takase, K. et al. (1992) Biochemica et Biophysica Acta, 1120:281–288; Matsui, I. et al. (1992) Febs Letters Vol. 310, No. 3, pp. 216–218); which residues are important for thermal stability (Suzuki, Y. et al. (1989) J. Biol. Chem. 264:18933–18938); and one group has used such methods to introduce mutations at various histidine residues in a *B. licheniformis* amylase, the rationale for making substitutions at histidine residues was that *B. licheniformis* amylase (known to be thermostable) when compared to other similar Bacillus amylases, has an excess of histidines and, therefore, it was suggested that replacing a histidine could affect the thermostability of the enzyme (Declerck, N. et al. (1990) J. Biol. Chem. 265:15481–15488; FR 2 665 178-A1; Joyet, P. et al. (1992) Bio/Technology 10:1579–1583).

It has been found that alpha-amylase is inactivated by hydrogen peroxide and other oxidants at pH's between 4 and 10.5 as described in the examples herein. Commercially, alpha-amylase enzymes can be used under dramatically different conditions such as both high and low pH conditions, depending on the commercial application. For example, alpha-amylases may be used in the liquefaction of starch, a process preferably performed at a low pH (pH <5.5). On the other hand, amylases may be used in commercial dish care or laundry detergents, which often contain oxidants such as bleach or peracids, and which are used in much more alkaline conditions.

In order to alter the stability or activity profile of amylase enzymes under varying conditions, it has been found that selective replacement, substitution or deletion of oxidizable amino acids, such as a methionine, tryptophan, tyrosine, histidine or cysteine, results in an altered profile of the variant enzyme as compared to its precursor. Because currently commercially available amylases are not acceptable (stable) under various conditions, there is a need for an amylase having an altered stability and/or activity profile. This altered stability (oxidative, thermal or pH performance profile) can be achieved while maintaining adequate enzymatic activity, as compared to the wild-type or precursor enzyme. The characteristic affected by introducing such mutations may be a change in oxidative stability while maintaining thermal stability or vice versa. Additionally, the substitution of different amino acids for an oxidizable amino acids in the alpha-amylase precursor sequence or the deletion of one or more oxidizable amino acid(s) may result in altered enzymatic activity at a pH other than that which is considered optimal for the precursor alpha-amylase. In other words, the mutant enzymes of the present invention may also have altered pH performance profiles, which may be due to the enhanced oxidative stability of the enzyme.

SUMMARY OF THE INVENTION

The present invention relates to novel alpha-amylase mutants that are the expression product of a mutated DNA sequence encoding an alpha-amylase, the mutated DNA sequence being derived from a precursor alpha-amylase by the deletion or substitution (replacement) of one or more oxidizable amino acid. In one preferred embodiment of the present invention the mutant result from substituting a different amino acid for one or more methionine residue(s) in the precursor alpha-amylase. In another embodiment of the present invention the mutants comprise a substitution of one or more tryptophan residue alone or in combination with the substitution of one or more methionine residue in the precursor alpha-amylase. Such mutant alpha-amylases, in general, are obtained by in vitro modification of a precursor DNA sequence encoding a naturally occurring or recombinant alpha-amylase to encode the substitution or deletion of one or more amino acid residues in a precursor amino acid sequence.

Preferably the substitution or deletion of one or more amino acid in the amino acid sequence is due to the replacement or deletion of one or more methionine, tryptophan, cysteine, histidine or tyrosine residues in such sequence, most preferably the residue which is changed is a methionine residue. The oxidizable amino acid residues may be replaced by any of the other 20 naturally occurring amino acids. If the desired effect is to alter the oxidative stability of the precursor, the amino acid residue may be substituted with a non-oxidizable amino acid (such as alanine, arginine, asparagine, aspartic acid, glutamic acid, glutamine, glycine, isoleucine, leucine, lysine, phenylalanine, proline, serine, threonine, or valine) or another oxidizable amino acid (such as cysteine, methionine, tryptophan, tyrosine or histidine, listed in order of most easily oxidizable to less readily oxidizable). Likewise, if the desired effect is to alter thermostability, any of the other 20 naturally occurring amino acids may be substituted (i.e., cysteine may be substituted for methionine).

Preferred mutants comprise the substitution of a methionine residue equivalent to any of the methionine residues found in *B. licheniformis* alpha-amylase (+8, +15, +197, +256, +304, +366 and +438). Most preferably the methionine to be replaced is a methionine at a position equivalent to position +197 or +15 in *B. licheniformis* alpha-amylase. Preferred substitute amino acids to replace the methionine at position +197 are alanine (A), isoleucine (I), threonine (T) or cysteine (C). The preferred substitute amino acids at position +15 are leucine (L), threonine (T), asparagine (N), aspartate (D), serine (S), valine (V) and isoleucine (I), although other substitute amino acids not specified above may be useful. Two specifically preferred mutants of the present invention are M197T and M15L.

Another embodiment of this invention relates to mutants comprising the substitution of a tryptophan residue equivalent to any of the tryptophan residues found in *B. licheniformis* alpha-amylase (see FIG. 2). Preferably the tryptophan to be replaced is at a position equivalent to +138 in *B. licheniformis* alpha-amylase. A mutation (substitution) at a tryptophan residue may be made alone or in combination with mutations at other oxidizable amino acid residues. Specifically, it may be advantageous to modify by substitution at least one tryptophan in combination with at least one methionine (for example, the double mutant +138/+197).

The alpha-amylase mutants of the present invention, in general, exhibit altered oxidative stability in the presence of hydrogen peroxide and other oxidants such as bleach or peracids, or, more specific, milder oxidants such as chloramine-T. Mutant enzymes having enhanced oxidative stability will be useful in extending the shelf life and bleach, perborate, percarbonate or peracid compatibility of amylases used in cleaning products. Similarly, reduced oxidative stability may be useful in industrial processes that require the rapid and efficient quenching of enzymatic activity. The mutant enzymes of the present invention may also demonstrate a broadened pH performance profile whereby mutants such as M15L show stability for low pH starch liquefaction and mutants such as M197T show stability at high pH cleaning product conditions. The mutants of the present invention may also have altered thermal stability whereby the mutant may have enhanced stability at either high or low temperatures. It is understood that any change (increase or decrease) in the mutant's enzymatic characteristic(s), as compared to its precursor, may be beneficial depending on the desired end use of the mutant alpha-amylase.

In addition to starch processing and cleaning applications, variant amylases of the present invention may be used in any application in which known amylases are used, for example, variant amylases can be used in textile processing, food processing, etc. Specifically, it is contemplated that a variant enzyme such as M197C, which is easily inactivated by oxidation, would be useful in a process where it is desirable to completely remove amylase activity at the end of the process, for example, in frozen food processing applications.

The preferred alpha-amylase mutants of the present invention are derived from a Bacillus strain such as *B. licheniformis, B. amyloliquefaciens,* and *B. stearothermophilus*, and most preferably from *Bacillus licheniformis*.

In another aspect of the present invention there is provided a novel form of the alpha-amylase normally produced by *B. licheniformis*. This novel form, designated as the A4 form, has an additional four alanine residues at the N-terminus of the secreted amylase. (FIG. 4b.) Derivatives or mutants of the A4 form of alpha-amylase are encompassed within the present invention. By derivatives or mutants of the A4 form, it is meant that the present invention comprises the A4 form alpha-amylase containing one or more additional mutations such as, for example, mutation (substitution, replacement or deletion) of one or more oxidizable amino acid(s).

In a composition embodiment of the present invention there are provided detergent compositions, liquid, gel or granular, comprising the alpha-amylase mutants described herein. Particularly preferred are detergent compositions comprising a +197 position mutant either alone or in combination with other enzymes such as endoglycosidases, cellulases, proteases, lipases or other amylase enzymes. Additionally, it is contemplated that the compositions of the present invention may include an alpha-amylase mutant having more than one site-specific mutation.

In yet another composition embodiment of the present invention there are provided compositions useful in starch processing and particularly starch liquefaction. The starch liquefaction compositions of the present invention preferably comprise an alpha-amylase mutant having a substitution or deletion at position M15. Additionally, it is contemplated that such compositions may comprise additional components as known to those skilled in the art, including, for example, antioxidants, calcium, ions, etc.

In a process aspect of the present invention there are provided methods for liquefying starch, and particularly granular starch slurries, from either a wet or dry milled process. Generally, in the first step of the starch degradation process, the starch slurry is gelatinized by heating at a relatively high temperature (up to about 110° C.). After the starch slurry is gelatinized it is liquefied and dextrinized using an alpha-amylase. The conditions for such liquefaction are described in commonly assigned U.S. patent applications Ser. Nos. 07/785,624 and 07/785,623 and U.S. Pat. No. 5,180,669, the disclosure of which are incorporated herein by reference. The present method for liquefying starch comprises adding to a starch slurry an effective amount of an alpha-amylase of the present invention, alone or in combination with additional excipients such as an antioxidant, and reacting the slurry for an appropriate time and temperature to liquefy the starch.

A further aspect of the present invention comprises the DNA encoding the mutant alpha-amylases of the present invention (including A4 form and mutants thereof) and expression vectors encoding the DNA as well as host cells transformed with such expression vectors.

BRIEF DESCRIPTION OF THE DRAWINGS

FIGS. 1A–1C show the DNA sequence of the gene for alpha-amylase from *B. licheniformis* (NCIB8061), Seq ID No 31, and deduced translation product as described in Gray, G. et al. (1986) J. Bacter. 166:635–643.

FIG. 2 shows the amino acid sequence of the mature alpha-amylase enzyme from *B. licheniformis* (NCIB8061), Seq ID No 32.

FIGS. 3A–3B show an alignment of primary structures of Bacillus alpha-amylases. The *B. licheniformis* amylase (Am-Lich), Seq ID No 33, is described by Gray, G. et al. (1986) J. Bact. 166:635–643; the *B. amyloliquefaciens* amylase (Am-Amylo), Seq ID No 34, is described by Takkinen, K. et al. (1983) J. Biol. Chem. 258:1007–1013; and the *B. stearothermophilus* (Am-Stearo), Seq ID No 35, is described by Ihara, H. et al. (1985) J. Biochem. 98:95–103.

FIG. 4a shows the amino acid sequence of the mature alpha-amylase variant M197T, Seq ID No 36.

FIG. 4b shows the amino acid sequence of the A4 form of alpha-amylase from *B. licheniformis* NCIB8061, Seq ID No 37. Numbering is from the N-terminus, starting with the four additional alanines.

FIG. 5 shows plasmid pA4BL wherein BLAA refers to *B. licheniformis* alpha-amylase gene, PstI to SstI; AmP$^R$ refers to the ampicillin-resistant gene from pBR322; and CAT refers to the Chloramphenicol-resistant gene from pC194.

FIG. 6 shows the signal sequence-mature protein junctions for *B. licheniformis* (Seq ID No 38), *B. subtilis* (Seq ID No 39), *B. licheniformis* in pA4BL (Seq ID No 40) and *B. licheniformis* in pBLapr (Seq ID No 41).

FIG. 7a shows inactivation of certain alpha-amylases (Spezyme® AA20 and M197L (A4 form) with 0.88M $H_2O_2$ at pH 5.0, 25° C.

FIG. 7b shows inactivation of certain alpha-amylases (Spezyme® AA20, M197T) with 0.88M $H_2O_2$ at pH 10.0, 25° C.

FIG. 7c shows inactivation of certain alpha-amylases (Spezyme® AA20, M15L) with 0.88M $H_2O_2$ at pH 5.0, 25° C.

FIG. 8 shows a schematic for the production of M197X cassette mutants.

FIG. 9 shows expression of M197X variants.

FIG. 10 shows thermal stability of M197X variants at pH 5.0, 5 mM $CaCl_2$ at 95° C. for 5 mins.

FIGS. 11a and 11b show inactivation of certain amylases in automatic dish care detergents. FIG. 11a shows the stability of certain amylases in Cascade™ (a commercially available dish care product) at 65° C. in the presence or absence of starch. Fig. 11b shows the stability of certain amylases in Sunlight™ (a commercially available dish care product) at 65° C. in the presence or absence of starch.

FIG. 12 shows a schematic for the production of M15X cassette mutants.

FIG. 13 shows expression of M15X variants.

FIG. 14 shows specific activity of M15X variants on soluble starch.

FIG. 15 shows heat stability of M15X variants at 90° C., pH 5.0, 5 mM $CaCl_2$, 5 mins.

FIG. 16 shows specific activity on starch and soluble substrate, and performance in jet liquefaction at pH 5.5, of M15 variants as a function of percent activity of *B. licheniformis* wild-type.

FIG. 17 shows the inactivation of *B. licheniformis* alpha-amylase (AA20 at 0.65 mg/ml) with chloramine-T at pH 8.0 as compared to variants M197A (1.7 mg/ml) and M197L (1.7 mg/ml).

FIG. 18 shows the inactivation of *B. licheniformis* alpha-amylase (AA20 at 0.22 mg/ml) with chloramine-T at pH 4.0 as compared to variants M197A (4.3 mg/ml) and M197L (0.53 mg/ml).

FIG. 19 shows the reaction of *B. licheniformis* alpha-amylase (AA20 at 0.75 mg/ml) with chloramine-T at pH 5.0 as compared to double variants M197T/W138F (0.64 mg/ml) and M197T/W138Y (0.60 mg/ml).

DETAILED DESCRIPTION OF THE INVENTION

It is believed that amylases used in starch liquefaction may be subject to some form of inactivation due to some activity present in the starch slurry (see commonly owned U.S. applications Ser. Nos. 07/785,624 and 07/785,623 and U.S. Pat. No. 5,180,669, issued Jan. 19, 1993, incorporated herein by reference). Furthermore, use of an amylase in the presence of oxidants, such as in bleach or peracid containing detergents, may result in partial or complete inactivation of the amylase. Therefore, the present invention focuses on altering the oxidative sensitivity of amylases. The mutant enzymes of the present invention may also have an altered pH profile and/or altered thermal stability which may be due to the enhanced oxidative stability of the enzyme at low or high pH's.

Alpha-amylase as used herein includes naturally occurring amylases as well as recombinant amylases. Preferred amylases in the present invention are alpha-amylases derived from *B. licheniformis* or *B. stearothermophilus*, including the A4 form of alpha-amylase derived from *B. lichenifromis* as described herein, as well as fungal alpha-amylases such as those derived from Aspergillus (i.e., *A. oryzae* and *A. niger*).

Recombinant alpha-amylases refers to an alpha-amylase in which the DNA sequence encoding the naturally occurring alpha-amylase is modified to produce a mutant DNA sequence which encodes the substitution, insertion or deletion of one or more amino acids in the alpha-amylase sequence. Suitable modification methods are disclosed herein, and also in commonly owned U.S. Pat. Nos. 4,760,025 and 5,185,258, the disclosure of which are incorporated herein by reference.

Homologies have been found between almost all endo-amylases sequenced to date, ranging from plants, mammals, and bacteria (Nakajima, R. T. et al. (1986) Appl. Microbiol. Biotechnol. 23:355–360; Rogers, J. C. (1985) Biochem. Biophys. Res. Commun. 128:470–476). There are four areas of particularly high homology in certain Bacillus amylases, as shown in FIG. 3, wherein the underlined sections designate the areas of high homology. Further, sequence alignments have been used to map the relationship between Bacillus endo-amylases (Feng, D. F. and Doolittle, R. F. (1987) J. Molec. Evol. 35:351–360). The relative sequence homology between *B. stearothermophilus* and *B. lichenifor-mis* amylase is about 66%, as determined by Holm, L. et al. (1990) Protein Engineering 3 (3) pp.181–191. The sequence homology between *B. licheniformis* and *B. amyloliquefaciens* amylases is about 81%, as per Holm, L. et al., supra. While sequence homology is important, it is generally recognized that structural homology is also important in comparing amylases or other enzymes. For example, structural homology between fungal amylases and bacterial (Bacillus) amylase have been suggested and, therefore, fungal amylases are encompassed within the present invention.

An alpha-amylase mutant has an amino acid sequence which is derived from the amino acid sequence of a precursor alpha-amylase. The precursor alpha-amylases include naturally occurring alpha-amylases and recombinant alpha-amylases (as defined). The amino acid sequence of the alpha-amylase mutant is derived from the precursor alpha-amylase amino acid sequence by the substitution, deletion or insertion of one or more amino acids of the precursor amino acid sequence. Such modification is of the precursor DNA sequence which encodes the amino acid sequence of the precursor alpha-amylase rather than manipulation of the precursor alpha-amylase enzyme per se. Suitable methods for such manipulation of the precursor DNA sequence include methods disclosed herein and in commonly owned U.S. Pat. Nos. 4,760,025 and 5,185,258.

Specific residues corresponding to positions M197, M15 and W138 of *Bacillus licheniformis* alpha-amylase are identified herein for substitution or deletion, as are all methionine, histidine, tryptophan, cysteine and tyrosine positions. The amino acid position number (i.e., +197) refers to the number assigned to the mature *Bacillus licheniformis* alpha-amylase sequence presented in FIG. 2. The invention, however, is not limited to the mutation of this particular mature alpha-amylase (*B. licheniformis*) but extends to precursor alpha-amylases containing amino acid residues at positions which are equivalent to the particular identified residue in *B. licheniformis* alpha-amylase. A residue (amino acid) of a precursor alpha-amylase is equivalent to a residue of *B. licheniformis* alpha-amylase if it is either homologous (i.e., corresponding in position in either primary or tertiary structure) or analogous to a specific residue or portion of that residue in *B. licheniformis* alpha-amylase (i.e., having the same or similar functional capacity to combine, react, or interact chemically or structurally).

In order to establish homology to primary structure, the amino acid sequence of a precursor alpha-amylase is directly compared to the *B. licheniformis* alpha-amylase primary sequence and particularly to a set of residues known to be invariant to all alpha-amylases for which sequence is known, as seen in FIG. 3. It is possible also to determine equivalent residues by tertiary structure: crystal structures have been reported for porcine pancreatic alpha-amylase (Buisson, G. et al. (1987) EMBO J. 6:3909–3916); Taka-amylase A from *Aspergillus oryzae* (Matsuura, Y. et al. (1984) J. Biochem. (Tokyo) 95:697–702); and an acid alpha-amylase from *A. niger* (Boel, E. et al. (1990) Biochemistry 29:6244–6249), with the former two structures being similar. There are no published structures for Bacillus alpha-amylases, although there are predicted to be common super-secondary structures between glucanases (MacGregor, E. A. & Svensson, B. (1989) Biochem. J. 259:145–152) and a structure for the *B. stearothermophilus* enzyme has been modeled on that of Taka-amylase A (Holm, L. et al. (1990) Protein Engineering 3:181–191). The four highly conserved regions shown in FIG. 3 contain many residues thought to be part of the active-site (Matsuura, Y. et al. (1984) J. Biochem. (Tokyo) 95:697–702; Buisson, G. et al. (1987) EMBO J. 6:3909–3916; Vihinen, M. et al. (1990) J. Biochem. 107:267–272) including, in the *licheniformis* numbering, His105; Arg229; Asp231; His235; Glu261 and Asp328.

Expression vector as used herein refers to a DNA construct containing a DNA sequence which is operably linked to a suitable control sequence capable of effecting the expression of said DNA in a suitable host. Such control sequences may include a promoter to effect transcription, an optional operator sequence to control such transcription, a sequence encoding suitable mRNA ribosome-binding sites, and sequences which control termination of transcription and translation. A preferred promoter is the *B. subtilis* aprE promoter. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art.

Host strains (or cells) useful in the present invention generally are procaryotic or eucaryotic hosts and include any transformable microorganism in which the expression of alpha-amylase can be achieved. Specifically, host strains of the same species or genus from which the alpha-amylase is derived are suitable, such as a Bacillus strain. Preferably an alpha-amylase negative Bacillus strain (genes deleted) and/or an alpha-amylase and protease deleted Bacillus strain such as *Bacillus subtilis* strain BG2473 (ΔamyE,Δapr,Δnpr) is used. Host cells are transformed or transfected with vectors constructed using recombinant DNA techniques. Such transformed host cells are capable of either replicating vectors encoding the alpha-amylase and its variants (mutants) or expressing the desired alpha-amylase.

Preferably the mutants of the present invention are secreted into the culture medium during fermentation. Any suitable signal sequence, such as the aprE signal peptide, can be used to achieve secretion.

Many of the alpha-amylase mutants of the present invention are useful in formulating various detergent compositions, particularly certain dish care cleaning compositions, especially those cleaning compositions containing known oxidants. Alpha-amylase mutants of the invention can be formulated into known powdered, liquid or gel detergents having pH between 6.5 to 12.0. Suitable granular composition may be made as described in commonly owned U.S. patent applications Ser. Nos. 07/429,881, 07/533,721 and 07/957,973, all of which are incorporated herein by reference. These detergent cleaning compositions can also contain other enzymes, such as known proteases, lipases, cellulases, endoglycosidases or other amylases, as well as builders, stabilizers or other excipients known to those skilled in the art. These enzymes can be present as co-granules or as blended mixes or in any other manner known to those skilled in the art. Furthermore, it is contemplated by the present invention that multiple mutants may be useful in cleaning or other applications. For example, a mutant enzyme having changes at both +15 and +197 may exhibit enhanced performance useful in a cleaning product or a multiple mutant comprising changes at +197 and +138 may have improved performance.

As described previously, alpha-amylase mutants of the present invention may also be useful in the liquefaction of starch. Starch liquefaction, particularly granular starch slurry liquefaction, is typically carried out at near neutral pH's and high temperatures. As described in commonly owned U.S. applications Ser. Nos. 07/788,624 and 07/785,623 and U.S. Pat. No. 5,180,669, it appears that an oxidizing agent or inactivating agent of some sort is also present in typical liquefaction processes, which may affect the enzyme activity; thus, in these related patent applications an anti-oxidant is added to the process to protect the enzyme.

Based on the conditions of a preferred liquefaction process, as described in commonly owned U.S. applications Ser. Nos. 07/788,624 and 07/785,623 and U.S. Pat. No. 5,180,669, namely low pH, high temperature and potential oxidation conditions, preferred mutants of the present invention for use in liquefaction processes comprise mutants exhibiting altered pH performance profiles (i.e., low pH profile, pH <6 and preferably pH <5.5), and/or altered thermal stability (i.e., high temperature, about 90°–110° C.), and/or altered oxidative stability (i.e., enhanced oxidative stability).

Thus, an improved method for liquefying starch is taught by the present invention, the method comprising liquefying a granular starch slurry from either a wet or dry milling process at a pH from about 4 to 6 by adding an effective amount of an alpha-amylase mutant of the present invention to the starch slurry; optionally adding an effective amount of an antioxidant or other excipient to the slurry; and reacting the slurry for an appropriate time and temperature to liquefy the starch.

The following is presented by way of example and is not to be construed as a limitation to the scope of the claims. Abbreviations used herein, particularly three letter or one letter notations for amino acids are described in Dale, J. W., Molecular Genetics of Bacteria, John Wiley & Sons, (1989) Appendix B.

Experimental

EXAMPLE 1

Substitutions for the Methionine Residues in *B. licheniformis* Alpha-Amvlase

The alpha-amylase gene (FIG. 1) was cloned from *B. licheniformis* NCIB8061 obtained from the National Collection of Industrial Bacteria, Aberdeen, Scotland (Gray, G. et al. (1986) J. Bacteriology 166:635–643). The 1.72 kb PstI-SstI fragment, encoding the last three residues of the signal sequence; the entire mature protein and the terminator region was subcloned into M13MP18. A synthetic terminator was added between the BclI and SstI sites using a synthetic oligonucleotide cassette of the form:

```
BclI                                                                    SstI

5'    GATCAAAACATAAAAAACCGGCCTTGGCCCCGCCGGTTTTTTATTATTTTTGAGCT   3'    Seq ID No 1

3'           TTTTGTATTTTTTGGCCGGAACCGGGGCGGCCAAAAAATAATAAAAAC          5'
``` designed to contain the *B. amyloliquefaciens* subtilisin transcriptional terminator (Wells et al. (1983) Nucleic Acid Research 11:7911–7925).

Site-directed mutagenesis by oligonucleotides used essentially the protocol of Zoller, M. et al. (1983) Meth. Enzymol. 100:468–500: briefly, 5'-phosphorylated oligonucleotide primers were used to introduce the desired mutations on the M13 single-stranded DNA template using the oligonucleotides listed in Table I to substitute for each of the seven methionines found in *B. licheniformis* alpha-amylase. Each mutagenic oligonucleotide also introduced a restriction endonuclease site to use as a screen for the linked mutation.

Following the methods described in U.S. application 860,468 (Power et al.), which is incorporated herein by reference, a silent PstI site was introduced at codon +1 (the first amino-acid following the signal cleavage site) of the aprE gene from pS168-1 (Stahl, M. L. and Ferrari, E. (1984) J. Bacter. 158:411–418). The aprE promoter and signal peptide region was then cloned out of a pJH101 plasmid (Ferrari, F. A. et al. (1983) J. Bacter. 154:1513–1515) as a HindIII-PstI fragment and subcloned into the pUC18-derived plasmid JM102 (Ferrari, E. and Hoch, J. A. (1989) Bacillus, ed. C. R. Harwood, Plenum Pub., pp. 57–72). Addition of the PstI-SstI fragment from *B. licheniformis*

TABLE I

Mutagenic Oligonucleotides for the Substitution of the Methionine Residues in *B. licheniformis*Alpha-Amylase

```
                  M8A
5'-T GGG ACG CTG GCG CAG TAC TTT GAA TGG TGG T-3'          Seq ID No 2
                    ScaI+

M15L
5'-TG ATG CAG TAC TTT GAA TGG TAC CTG CCC AAT GA-3'        Seq ID No 3
          ScaI+        KpnI+

M197L
5'-GAT TAT TTG TTG TAT GCC GAT ATC GAC TAT GAC CAT-3'      Seq ID No 4
                         EcoRV+

M256A
5'-CG GGG AAG GAG GCC TTT ACG GTA GCT-3'                   Seq ID No 5
            StuI+

M304L
5'-GC GGC TAT GAC TTA AGG AAA TTG C-3'                     Seq ID No 6
              AfIII+

M366A
5'-C TAC GGG GAT GCA TAC GGG ACG A-3'                      Seq ID No 7
           NsiI+

M366Y
5'-C TAC GGG GAT TAC TAC GGG ACC AAG GGA GAC TCC C-3'      Seq ID No 8
                         StyI+

M438A
5'-CC GGT GGG GCC AAG CGG GCC TAT GTT GGC CGG CAA A-3'     Seq ID No 9
          SfiI+
```

Bold letter indicate base changes introduced by oligonucleotide.

Codon changes indicated in the form M8A, where methionine (M) at position +8 has been changed to alanine (A).

Underlining indicates restriction endonuclease site introduced by oligonucleotide.

The heteroduplex was used to transfect *E. coli* mutL cells (Kramer et al. (1984) Cell 38:879) and, after plaque-purification, clones were analyzed by restriction analysis of the RF1's. Positives were confirmed by dideoxy sequencing (Sanger et al. (1977) Proc. Natl. Acad. Sci. U.S.A. 74:5463–5467) and the PstI-SstI fragments for each subcloned into an *E. coli* vector, plasmid pA4BL.

Plasmid PA4BL alpha-amylase gave pA4BL (FIG. 5) having the resulting aprE signal peptide-amylase junction as shown in FIG. 6.

Transformation Into *B. subtilis* pA4BL is a plasmid able to replicate in *E. coli* and integrate into the *B. subtilis* chromosome. Plasmids containing different variants were transformed into *B. subtilis* (Anagnostopoulos, C. and Spizizen, J. (1961) J. Bacter. 81:741–746) and integrated into the chromosome at the aprE locus by a Campbell-type mechanism (Young, M. (1984) J. Gen. Microbiol. 130:1613–1621). The *Bacillus subtilis* strain BG2473 was a derivative of I168 which had been deleted for amylase (ΔamyE) and two proteases (Δapr, Δnpr) (Stahl, M. L. and Ferrari, E., J. Bacter. 158:411–418 and U.S. Pat. No. 5,264,366, incorporated herein by reference). After transformation the sacU32(Hy) (Henner, D. J. et al. (1988) J. Bacter. 170:296–300) mutation was introduced by PBS-1 mediated transduction (Hoch, J. A. (1983) 154:1513–1515).

N-terminal analysis of the amylase expressed from pA4BL in *B. subtilis* showed it to be processed having four extra alanines at the N-terminus of the secreted amylase protein ("A4 form"). These extra residues had no significant, deleterious effect on the activity or thermal stability of the A4 form and in some applications may enhance performance. In subsequent experiments the correctly processed forms of the *licheniformis* amylase and the variant M197T were made from a very similar construction (see FIG. 6). Specifically, the 5' end of the A4 construction was subcloned on an EcoRI-SstII fragment, from pA4BL (FIG. 5) into M13BM20 (Boehringer Mannheim) in order to obtain a coding-strand template for the mutagenic oligonucleotide below:

5'-CAT CAG CGT CCC ATT AAG ATT TGC AGC CTG CGC AGA CAT GTT GCT-3' Seq ID No 10

This primer eliminated the codons for the extra four N-terminal alanines, correct forms being screened for by the absence of the PstI site. Subcloning the EcoRI-SstII fragment back into the pA4BL vector (FIG. 5) gave plasmid pBLapr. The M197T substitution could then be moved, on a SstII-SstI fragment, out of pA4BL (M197T) into the complementary pBLapr vector to give plasmid pBLapr (M197T). N-terminal analysis of the amylase expressed from pBLapr in *B. subtilis* showed it to be processed with the same N-terminus found in *B. licheniformis* alpha-amylase.

EXAMPLE 2

Oxidative Sensitivity of Methionine Variants

*B. licheniformis* alpha-amylase, such as Spezyme® AA20 (commercially available from Genencor International, Inc.), is inactivated rapidly in the presence of hydrogen peroxide (FIG. 7). Various methionine variants were expressed in shake-flask cultures of *B. subtilis* and the crude supernatants purified by ammonium sulphate cuts. The amylase was precipitated from a 20% saturated ammonium sulphate supernatant by raising the ammonium sulphate to 70% saturated, and then resuspended. The variants were then exposed to 0.88M hydrogen peroxide at pH 5.0, at 25° C. Variants at six of the methionine positions in *B. licheniformis* alpha-amylase were still subject to oxidation by peroxide while the substitution at position +197 (M197L) showed resistance to peroxide oxidation. (See FIG. 7.) However, subsequent analysis described in further detail below showed that while a variant may be susceptible to oxidation at pH 5.0, 25° C., it may exhibit altered/enhanced properties under different conditions (i.e., liquefaction).

EXAMPLE 3

Construction of All Possible Variants at Position 197

All of the M197 variants (M197X) were produced in the A4 form by cassette mutagenesis, as outlined in FIG. 8:
  1) Site directed mutagenesis (via primer extension in M13) was used to make M197A using the mutagenic oligonucleotide below:

```
       M197A
5'-GAT TAT TTG'GCG TAT GCC GAT ATC GAC TAT GAC CAT-3' Seq ID No 11
                           EcoRV+
                              ClaI-
``` which also inserted an EcoRV site (codons 200–201) to replace the ClaI site (codons 201–202).
  2) Then primer LAAM12 (Table II) was used to introduce another silent restriction site (BstBI) over codons 186–188.
  3) The resultant M197A (BstBI+, EcoRV+) variant was then subcloned (PstI-SstI fragment) into plasmid pA4BL and the resultant plasmid digested with BstBI and EcoRV and the large vector-containing fragment isolated by electroelution from agarose gel.
  4) Synthetic primers LAAM14–30 (Table II) were each annealed with the largely complementary common primer LAAM13 (Table II). The resulting cassettes encoded for all the remaining naturally occurring amino acids at position +197 and were ligated, individually, into the vector fragment prepared above.

TABLE II

Synthetic Oligonucleotides Used for Cassette Mutagenesis to Produce M197X Variants

LAAM12 GG GAA GTT TCG AAT GAA AAC G    Seq ID No 12

LAAM13 X197bs    Seq ID No 13
(EcoRV) GTC GGC ATA TG  CAT ATA ATC'ATA GTT GCC GTT TTC ATT (BstBI)

LAAM14 I197    Seq ID No 14
(BstBI) CG AAT GAA AAC GGC AAC TAT GAT TAT TTG ATC TAT GCC GAC (EcoRV-)

LAAM15 F197    Seq ID No 15
(BstBI) CG AAT GAA AAC GGC AAC TAT GAT TAT TTG TTC TAT GCC GAC (EcoRV-)

TABLE II-continued

Synthetic Oligonucleotides Used for Cassette Mutagenesis
to Produce M197X Variants

| | | |
|---|---|---|
| LAAM16 V197 | | Seq ID No 16 |
| (BstBI) CG AAT GAA AAC GGC AAC TAT GAT TAT TTG GTT TAT GCC GAC (EcoRV-) | | |
| LAAM17 S197 | | Seq ID No 17 |
| (BstBI) CG AAT GAA AAC GGC AAC TAT GAT TAT TTG AGC TAT GCC GAC (EcoRV-) | | |
| LAAM18 P197 | | Seq ID No 18 |
| (BstBI) CG AAT GAA AAC GGC AAC TAT GAT TAT TTG CCT TAT GCC GAC (EcoRV-) | | |
| LAAM19 T197 | | Seq ID No 19 |
| (BstBI) CG AAT GAA AAC GGC AAC TAT GAT TAT TTG ACA TAT GCC GAC (EcoRV-) | | |
| LAAM20 Y197 | | Seq ID No 20 |
| (BstBI) CG AAT GAA AAC GGC AAC TAT GAT TAT TTG TAC TAT GCC GAC (EcoRV-) | | |
| LAAM21 H197 | | Seq ID No 21 |
| (BstBI) CG AAT GAA AAC GGC AAC TAT GAT TAT TTG CAC TAT GCC GAC (EcoRV-) | | |
| LAAM22 G197 | | Seq ID No 22 |
| (BstBI) CG AAT GAA AAC GGC AAC TAT GAT TAT TTG GGC TAT GCC GAC (EcoRV-) | | |
| LAAM23 Q197 | | Seq ID No 23 |
| (BstBI) CG AAT GAA AAC GGC AAC TAT GAT TAT TTG CAA TAT GCC GAC (EcoRV-) | | |
| LAAM24 N197 | | Seq ID No 24 |
| (BstBI) CG AAT GAA AAC GGC AAC TAT GAT TAT TTG AAC TAT GCC GAC (EcoRV-) | | |
| LAAM25 K197 | | Seq ID No 25 |
| (BstBI) CG AAT GAA AAC GGC AAC TAT GAT TAT TTG AAA TAT GCC GAC (EcoRV-) | | |
| LAAM26 D197 | | Seq ID No 26 |
| (BstBI) CG AAT GAA AAC GGC AAC TAT GAT TAT TTG GAT TAT GCC GAC (EcoRV-) | | |
| LAAM27 E197 | | Seq ID No 27 |
| (BstBI) CG AAT GAA AAC GGC AAC TAT GAT TAT TTG GAA TAT GCC GAC (EcoRV-) | | |
| LAAM28 C197 | | Seq ID No 28 |
| (BstBI) CG AAT GAA AAC GGC AAC TAT GAT TAT TTG TGT TAT GCC GAC (EcoRV-) | | |
| LAAM29 W197 | | Seq ID No 29 |
| (BstBI) CG AAT GAA AAC GGC AAC TAT GAT TAT TTG TGG TAT GCC GAC (EcoRV-) | | |
| LAAM30 R197 | | Seq ID No 30 |
| (BstBI) CG AAT GAA AAC GGC AAC TAT GAT TAT TTG AGA TAT GCC GAC (EcoRV-) | | |

The cassettes were designed to destroy the EcoRV site upon ligation, thus plasmids from *E. coli* transformants were screened for loss of this unique site. In addition, the common bottom strand of the cassette contained a frame-shift and encoded a NsiI site, thus transformants derived from this strand could be eliminated by screening for the presence of the unique NsiI site and would not be expected, in any case, to lead to expression of active amylase.

Positives by restriction analysis were confirmed by sequencing and transformed in *B. subtilis* for expression in shake-flask cultures (FIG. 9). The specific activity of certain of the M197X mutants was then determined using a soluble substrate assay. The data generated using the following assay methods are presented below in Table III.

Soluble Substrate Assay

A rate assay was developed based on an end-point assay kit supplied by Megazyme (Aust.) Pty. Ltd.: Each vial of substrate (p-nitrophenyl maltoheptaoside, BPNPG7) was dissolved in 10 ml of sterile water, followed by a 1 to 4 dilution in assay buffer (50 mM maleate buffer, pH 6.7, 5 mM calcium chloride, 0.002% Tween20). Assays were performed by adding 10 µl of amylase to 790 µl of the substrate in a cuvette at 25° C. Rates of hydrolysis were measured as the rate of change of absorbance at 410 nm, after a delay of 75 seconds. The assay was linear up to rates of 0.4 absorption units/min.

The amylase protein concentration was measured using the standard Bio-Rad assay (Bio-Rad Laboratories) based on the method of Bradford, M. (1976) Anal. Biochem. 72:248) using bovine serum albumin standards.

Starch Hydrolysis Assay

The standard method for assaying the alpha-amylase activity of Spezyme® AA20 was used. This method is described in detail in Example 1 of U.S. Ser. No. 07/785,624, incorporated herein by reference. Native starch forms a blue color with iodine but fails to do so when it is hydrolyzed into shorter dextrin molecules. The substrate is soluble Lintner starch 5 gm/liter in phosphate buffer, pH 6.2 (42.5 gm/liter potassium dihydrogen phosphate, 3.16 gm/liter sodium hydroxide). The sample is added in 25 mM calcium chloride and activity is measured as the time taken to give a negative iodine test upon incubation at 30° C. Activity is recorded in liquefons per gram or ml (LU) calculated according to the formula:

$$LU/\text{ml or } LU/g = \frac{570}{V \times t} \times D$$

Where LU=liquefon unit

V=volume of sample (5 ml)
t=dextrinization time (minutes)
D=dilution factor=dilution volume/ml or g of added enzyme.

TABLE III

| ALPHA-AMYLASE | SPECIFIC ACTIVITY (as % of AA20 value) on: | |
|---|---|---|
|  | Soluble Substrate | Starch |
| Spezyme ® AA20 | 100 | 100 |
| A4 form | 105 | 115 |
| M15L (A4 form) | 93 | 94 |
| M15L | 85 | 103 |
| M197T (A4 form) | 75 | 83 |
| M197T | 62 | 81 |
| M197A (A4 form) | 88 | 89 |
| M197C | 85 | 85 |
| M197L (A4 form) | 51 | 17 |

EXAMPLE 4

Characterization of Variant M15L

Variant M15L made as per the prior examples did not show increased amylase activity (Table III) and was still inactivated by hydrogen peroxide (FIG. 7). It did, however, show significantly increased performance in jet-liquefaction of starch, especially at low pH as shown in Table IV below.

Starch liquefaction was typically performed using a Hydroheater M 103-M steam jet equipped with a 2.5 liter delay coil behind the mixing chamber and a terminal back pressure valve. Starch was fed to the jet by a Moyno pump and steam was supplied by a 150 psi steam line, reduced to 90–100 psi. Temperature probes were installed just after the Hydroheater jet and just before the back pressure valve.

Starch slurry was obtained from a corn wet miller and used within two days. The starch was diluted to the desired solids level with deionized water and the pH of the starch was adjusted with 2% NaOH or saturated $Na_2CO_3$. Typical

```
M15XBstB1    5'-G ATG CAG TAT TTC GAA CTGG TAT A-3'     Seq ID No 48
                                  BstB1

M15CMsc1     5'-TG CCC AAT GAT GGC CAA CAT TGG AAG-3'    Seq ID No 49
                              Msc1
``` liquefaction conditions were:

| Starch | 32%–35% solids |
|---|---|
| Calcium | 40–50 ppm (30 ppm added) |
| pH | 5.0–6.0 |
| Alpha-amylase | 12–14 LU/g starch dry basis |

Starch was introduced into the jet at about 350 ml/min. The jet temperature was held at 105°–107° C. Samples of starch were transferred from the jet cooker to a 95° C. second stage liquefaction and held for 90 minutes.

The degree of starch liquefaction was measured immediately after the second stage liquefaction by determining the dextrose equivalence (DE) of the sample and by testing for the presence of raw starch, both according to the methods described in the *Standard Analytical Methods of the Member Companies of the Corn Refiners Association, Inc.*, sixth edition. Starch, when treated generally under the conditions given above and at pH 6.0, will yield a liquefied starch with a DE of about 10 and with no raw starch. Results of starch liquefaction tests using mutants of the present invention are provided in Table IV.

TABLE IV

| Performance of Variants M15L (A4 form) and M15L in Starch Liquefaction | | |
|---|---|---|
|  | pH | DE after 90 Mins. |
| Spezyme ® AA20 | 5.9 | 9.9 |
| M15L (A4 form) | 5.9 | 10.4 |
| Spezyme ® AA20 | 5.2 | 1.2 |
| M15L (A4 form) | 5.2 | 2.2 |
| Spezyme ® AA20 | 5.9 | 9.3* |
| M15L | 5.9 | 11.3* |
| Spezyme ® AA20 | 5.5 | 3.25** |
| M15L | 5.5 | 6.7** |
| Spezyme ® AA20 | 5.2 | 0.7** |
| M15L | 5.2 | 3.65** |

*average of three experiments
**average of two experiments

EXAMPLE 5

Construction of M15X Variants

Following generally the processes described in Example 3 above, all variants at M15 (M15X) were produced in native *B. licheniformis* by cassette mutagenesis, as outlined in FIG. 12:

1) Site directed mutagenesis (via primer extension in M13) was used to introduce unique restriction sites flanking the M15 codon to facilitate insertion of a mutagenesis cassette. Specifically, a BstB1 site at codons 11–13 and a Msc1 site at codons 18–20 were introduced using the two oligonucleotides shown below.

2) The vector for M15X cassette mutagenesis was then constructed by subcloning the Sfi1-SstII fragment from the mutagenized amylase (BstB1+, Msc1+) into plasmid pBLapr. The resulting plasmid was then digested with BstB1and Msc1 and the large vector fragment isolated by electroelution from a polyacrylamide gel.

3) Mutagenesis cassettes were created as with the M197X variants. Synthetic oligomers, each encoding a substitution at codon 15, were annealed to a common bottom primer. Upon proper ligation of the cassette to the vector, the Msc1 is destroyed allowing for screening of positive transformants by loss of this site. The bottom primer contains an unique SnaB1site allowing for the transformants derived from the bottom strand to be eliminated by screening for the SnaB1site. This primer also contains a frameshift which would also eliminate amylase expression for the mutants derived from the common bottom strand.

The synthetic cassettes are listed in Table V and the general cassette mutagenesis strategy is illustrated in FIG. 12.

TABLE V

Synthetic Oligonucleotides Used for Cassette Mutagenesis
to Produce M15X Variants

| | |
|---|---|
| M15A (BstB1) C GAA TGG TAT GCT CCC AAT GAC GG (Msc1) | Seq ID No 50 |
| M15R (BstB1) C GAA TGG TAT CGC CCC AAT GAC GG (Msc1) | Seq ID No 51 |
| M15N (BstB1) C GAA TGG TAT AAT CCC AAT GAC GG (Msc1) | Seq ID No 52 |
| M15D (BstB1) C GAA TGG TAT GAT CCC AAT GAC GG (Msc1) | Seq ID No 53 |
| M15H (BstB1) C GAA TGG TAT CAC CCC AAT GAC GG (Msc1) | Seq ID No 54 |
| M15K (BstB1) C GAA TGG TAT AAA CCC AAT GAC GG (Msc1) | Seq ID No 55 |
| M15P (BstB1) C GAA TGG TAT CCG CCC AAT GAC GG (Msc1) | Seq ID No 56 |
| M15S (BstB1) C GAA TGG TAT TCT CCC AAT GAC GG (Msc1) | Seq ID No 57 |
| M15T (BstB1) C GAA TGG TAT ACT CCC AAT GAC GG (Msc1) | Seq ID No 58 |
| M15V (BstB1) C GAA TGG TAT GTT CCC AAT GAC GG (Msc1) | Seq ID No 59 |
| M15C (BstB1) C GAA TGG TAT TGT CCC AAT GAC GG (Msc1) | Seq ID No 60 |
| M15Q (BstB1) C GAA TGG TAT CAA CCC AAT GAC GG (Msc1) | Seq ID No 61 |
| M15E (BstB1) C GAA TGG TAT GAA CCC AAT GAC GG (Msc1) | Seq ID No 62 |
| M15G (BstB1) C GAA TGG TAT GGT CCC AAT GAC GG (Msc1) | Seq ID No 63 |
| M15I (BstB1) C GAA TGG TAT ATT CCC AAT GAC GG (Msc1) | Seq ID No 64 |
| M15F (BstB1) C GAA TGG TAT TTT CCC AAT GAC GG (Msc1) | Seq ID No 65 |
| M15W (BstB1) C GAA TGG TAT TGG CCC AAT GAC GG (Msc1) | Seq ID No 66 |
| M15Y (BstB1) C GAA TGG TAT TAT CCC AAT GAC GG (Msc1) | Seq ID No 67 |
| M15X (Msc1) CC GTC ATT GGG ACT ACG TAC CAT T (BstB1) (bottom strand) | Seq ID No 68 |

Underline indicates codon changes at amino acid position 15.

Conservative substitutions were made in some cases to prevent introduction of new restriction sites.

EXAMPLE 6

Bench Liquefaction with M15X Variants

Eleven alpha-amylase variants with substitutions for M15 made as per Example 5 were assayed for activity, as compared to Spezyme® AA20 (commercially available from Genencor International, Inc.) in liquefaction at pH 5.5 using a bench liquefaction system. The bench scale liquefaction system consisted of a stainless steel coil (0.25 inch diameter, approximately 350 ml volume) equipped with a 7 inch long static mixing element approximately 12 inches from the anterior end and a 30 psi back pressure valve at the posterior end. The coil, except for each end, was immersed in a glycerol-water bath equipped with thermostatically controlled heating elements that maintained the bath at 105–106° C.

Starch slurry containing enzyme, maintained in suspension by stirring, was introduced into the reaction coil by a piston driven metering pump at about 70 ml/min. The starch was recovered from the end of the coil and was transferred to the secondary hold (95° C. for 90 minutes). Immediately after the secondary hold, the DE of the liquefied starch was determined, as described in Example 4. The results are shown in FIG. 16.

EXAMPLE 7

Characterization of M197X

As can be As can be seen in FIG. 9, there was a wide range of amylase activity (measured in the soluble substrate assay) expressed by the M197X (A4 form) variants. The amylases were partially purified from the supernatants by precipitation with two volumes of ethanol and resuspension. They were then screened for thermal stability (FIG. 10) by heating at 95° C. for 5 minutes in 10 mM acetate buffer pH 5.0, in the presence of 5 mM calcium chloride; the A4 wild-type retained 28% of its activity after incubation. For M197W and M197P we were unable to recover active protein from the supernatants. Upon sequencing, the M197H variant was found to contain a second mutation, NI90K. M197L was examined in a separate experiment and was one of the lowest thermally stable variants. There appears to be a broad correlation between expression of amylase activity and thermal stability. The licheniformis amylase is restricted in what residues it can accommodate at position 197 in terms of retaining or enhancing thermal stability: cysteine and threonine are preferred for maximal thermal stability under these conditions whereas alanine and isoleucine are of intermediate stability. However, other substitutions at position +197 result in lowered thermal stability which may be useful for other applications. Additionally, different substitutions at +197 may have other beneficial properties, such as altered pH performance profile or altered oxidative stability. For example, the M197C variant was found to inactivate readily by air oxidation but had enhanced thermal stability. Conversely, compared to the M197L variant, both M197T and M197A retained not only high thermal stability (FIG. 10), but also high activity (Table III), while maintaining resistance to inactivation by peroxide at pH 5 to pH 10 (FIG. 7).

EXAMPLE 8

Stability and Performance in Detergent Formulation

The stability of the M197T (A4 form), M197T and M197A (A4 form) was measured in automatic dish care detergent (ADD) matrices. 2 ppm Savinase™ (a protease, commercially available from Novo Industries, of the type commonly used in ADD) were added to two commercially available bleach-containing ADD's: Cascade™ (Procter and Gamble, Ltd.) and Sunlight™ (Unilever) and the time course of inactivation of the amylase variants and Termamyl™ (a thermally stable alpha-amylase available from Novo Nordisk, A/S) followed at 65° C. The concentration of ADD product used in both cases was equivalent to 'presoak' conditions: 14 gm product per liter of water (7 grams per gallon hardness). As can be seen (FIGS. 11a and 11b), both forms of the M197T variant were much more stable than Termamyl™ and M197A (A4 form), which were inactivated before the first assay could be performed. This stability benefit was seen in the presence or absence of starch as determined by the following protocol. Amylases were added to 5 ml of ADD and Savinase™, prewarmed in a test tube and, after vortexing, activities were assayed as a function of time, using the soluble substrate assay. The "+ starch" tube had spaghetti starch baked onto the sides (140° C., 60 mins.). The results are shown in FIGS. 11a and 11b.

EXAMPLE 9

Characterization of M15X Variants

All M15X variants were propagated in *Bacillus subtilis* and the expression level monitored as shown in FIG. 13. The amylase was isolated and partially purified by a 20–70% ammonium sulfate cut. The specific activity of these variants on the soluble substrate was determined as per Example 3 (FIG. 14). Many of the M15X amylases have specific activities greater than that of Spezyme® AA20. A benchtop heat stability assay was performed on the variants by heating the amylase at 90° C. for 5 min. in 50 mM acetate buffer pH 5 in the presence of 5 mM CaCl₂ (FIG. 15). Most of the variants performed as well as Spezyme® AA20 in this assay. Those variants that exhibited reasonable stability in this assay (reasonable stability defined as those that retained at least about 60% of Spezyme® AA20's heat stability) were tested for specific activity on starch and for liquefaction performance at pH 5.5. The most interesting of those mutants are shown in FIG. 16. M15D, N and T, along with L, outperformed Spezyme® AA20 in liquefaction at pH 5.5 and have increased specific activities in both the soluble substrate and starch hydrolysis assays.

Generally, we have found that by substituting for the methionine at position 15, we can provide variants with increased low pH-liquefaction performance and/or increased specific activity.

EXAMPLE 10

Tryptophan Sensitivity to Oxidation

Chloramine-T (sodium N-chloro-p-toluenesulfonimide) is a selective oxidant, which oxidizes methionine to methionine sulfoxide at neutral or alkaline pH. At acidic pH, chloramine-T will modify both methionine and tryptophan (Schechter, Y., Burstein, Y. and Patchomik, A. (1975) Biochemistry 14 (20) 4497–4503). FIG. 17 shows the inactivation of *B. licheniformis* alpha-amylase with chloramine-T at pH 8.0 (AA20=0.65 mg/ml, M197A=1.7 mg/ml, M197L= 1.7 mg/ml). The data shows that by changing the methionine at position 197 to leucine or alanine, the inactivation of alpha-amylase can be prevented. Conversely, as shown in FIG. 18, at pH 4.0 inactivation of the M197A and M197L proceeds, but require more equivalents of chloramine-T (FIG. 18; AA20=0.22 mg/ml, M197A=4.3 mg/ml, M197L= 0.53 mg/ml; 200 mM NaAcetate at pH 4.0). This suggests that a tryptophan residue is also implicated in the chloramine-T mediated inactivation event. Furthermore, tryptic mapping and subsequent amino acid sequencing indicated that the tryptophan at position 138 was oxidized by chloramine-T (data not shown). To prove this, site-directed mutants were made at tryptophan 138 as provided below: Preparation of Alpha-Amylase Double Mutants W138 and M197

Certain variants of W138 (F, Y and A) were made as double mutants, with M197T (made as per the disclosure of Example 3). The double mutants were made following the methods described in Examples 1 and 3. Generally, single negative strands of DNA were prepared from an M13MP18 clone of the 1.72 kb coding sequence (Pst I-Sst I) of the *B. licheniformis* alpha-amylase M197T mutant. Site-directed mutagenesis was done using the primers listed below, essentially by the method of Zoller, M. et al. (1983) except T4 gene 32 protein and T4 polymerase were substituted for klenow. The primers all contained unique sites, as well as the desired mutation, in order to identify those clones with the appropriate mutation.

```
Tryptophan 138 to Phenylalanine 133 134 135 136 137 138 139 140 141 142 143            Seq ID No 42
CAC CTA ATT AAA GCT TTC ACA CAT TTT CAT TTT
              Hind III Tryptophan 138 to Tyrosine 133 134 135 136 137 138 139 140 141 142 143            Seq ID No 43
CAC CTA ATT AAA GCT TAC ACA CAT TTT CAT TTT
              Hind III Tryptophan 138 to Alanine - This primer also engineers unique sites upstream and downstream of the 138 position.
```

```
                                                                                    -continued 127 128 129 130 131 132 133 134 135 136 137 138 139 140 141 142
C  CGC GTA ATT TCC GGA GAA CAC CTA ATT AAA GCC GCA ACA CAT TTT CAT
                 BspE I 143 144 145 146 147                                                    Seq ID No 44
TTT CCC GGG CGC GGC AG
    Xma I
```

Mutants were identified by restriction analysis and W138F and W138Y confirmed by DNA sequencing. The W138A sequence revealed a nucleotide deletion between the unique BspE I and Xma I sites, however, the rest of the gene sequenced correctly. The 1.37 kb SstII/SstI fragment containing both W138X and M197T mutations was moved from M13MP18 into the expression vector pBLapr resulting in pBLapr (W138F, M197T) and pBLapr (W138Y, M197T). The fragment containing unique BspE I and Xma I sites was cloned into pBLapr (BspE I, Xma I, M197T) since it is useful for cloning cassettes containing other amino acid substitutions at position 138.

Single Mutations at Amino Acid Position 138

Following the general methods described in the prior examples, certain single variants of W138 (F, Y, L, H and C) were made.

The 1.24 kb Asp718-SstI fragment containing the M197T mutation in plasmid pBLapr (W138X, M197T) of Example 7 was replaced by the wild-type fragment with methionine at 197, resulting in pBLapr (W138F), pBLapr (W138Y) and pBLapr (BspE I, Xma I).

The mutants W138L, W138H and W138C were made by ligating synthetic cassettes into the pBLapr (BspE I, Xma I) vector using the following primers:

```
Tryptophan 138 to Leucine

CC GGA GAA CAC CTA ATT AAA GCC CTA ACA CAT TTT CAT TTT C   Seq ID No 45

Tryptophan 138 to Histidine

CC GGA GAA CAC CTA ATT AAA GCC CAC ACA CAT TTT CAT TTT C   Seq ID No 46

Tryptophan 138 to Cysteine

CC GGA GAA CAC CTA ATT AAA GCC TGC ACA CAT TTT CAT TTT C   Seq ID No 47
```

Reaction of the double mutants M197T/W138F and M197T/W138Y with chloramine-T was compared with wild-type (AA20=0.75 mg/ml, M197T/W138F=0.64 mg/ml, M197T/W138Y=0.60 mg/ml; 50 mM NaAcetate at pH 5.0). The results shown in FIG. 19 show that mutagenesis of tryptophan 138 has caused the variant to be more resistant to chloramine-T.

What is claimed is:

1. A mutant alpha amylase derived from Bacillus, the mutant alpha amylase having a substitution of an amino acid selected from the group consisting of threonine, leucine, alanine, arginine, asparagine, aspartic acid, glutamic acid, glycine, isoleucine, lysine, phenylalanine, proline, serine, valine, histidine and glutamine or a deletion of a methionine residue at a position equivalent to M197 *Bacillus licheniformis* alpha amylase.

2. The mutant alpha-amylase of claim 1 which is M197T.

3. A mutant alpha-amylase of claim 1 wherein the precursor is selected from the group *B. licheniformis, B. stearothermophilus*, and *B. amyloliquefaciens*.

4. A mutant alpha-amylase of claim 3 wherein the precursor is *Bacillus licheniformis* alpha-amylase.

5. A detergent composition comprising a mutant alpha-amylase of claim 1.

6. A detergent composition of claim 5 which is a liquid, gel or granular composition.

7. A detergent composition of claim 5 further comprising one or more additional enzyme.

8. A starch liquefying composition comprising a mutant alpha-amylase of claim 1.

9. A mutant alpha amylase derived from Bacillus, the mutant alpha amylase having a substitution of an amino acid selected from the group consisting of leucine, threonine, asparagine, aspartate, serine, valine, and isoleucine for a methionine residue at a position equivalent to M15 in *Bacillus licheniformis* alpha amylase.

10. A mutant alpha-amylase of claim 9 wherein the precursor alpha-amylase is selected from the group consisting of *B. licheniformis, B. stearothermophilus* and *B. amyloliquefaciens*.

11. A mutant alpha-amylase of claim 10 wherein the precursor alpha-amylase is selected from *B. licheniformis*.

12. A mutant alpha-amylase of claim 9 further comprising the substitution or deletion of an amino acid residue in the precursor alpha amylase at a position equivalent to either or both of M197 or W138 in *Bacillus licheniformis* alpha-amylase.

13. A mutant alpha-amylase of claim 12 further comprising substitutions equivalent to M197T/W138F or M197T/W138Y in *Bacillus licheniformis* alpha-amylase.

14. A detergent composition comprising a mutant alpha-amylase of claim 9.

15. A detergent composition comprising a mutant alpha-amylase of claim 12.

16. A detergent composition of claim 15 which is a liquid, gel or granular composition.

17. A detergent composition of claim 16 which further comprises one or more additional enzymes.

18. A starch liquefying composition comprising a mutant alpha-amylase of claim 9.

19. A starch liquefying composition comprising a mutant alpha-amylase of claim 12.

20. The mutant alpha-amylase of claim 9 which is M15L.

21. The mutant alpha-amylase of claim 17 which is M15L.

22. An alpha-amylase comprising an amino acid sequence corresponding to SEQ ID No. 37.

23. A mutant alpha amylase derived from Bacillus, the mutant alpha amylase having at least two substitutions at positions equivalent to M15, W138 and/or M197 in *Bacillus licheniformis* alpha amylase, wherein said substitutions comprise M15T, W138Y and/or M197T.

24. A mutant alpha-amylase having enhanced oxidative stability, the mutant alpha-amylase being derived from Bacillus and comprising a substitution of methionine with alanine, arginine, glycine, lysine, phenylalanine, proline, threonine or valine at an amino acid residue equivalent to M197 in *Bacillus licheniformis* alpha-amylase.

25. A mutant alpha-amylase according to claim 24, said substitution comprising substituting methionine with threonine at an amino acid residue equivalent to M197 in *Bacillus licheniformis* alpha-amylase.

* * * * *

UNITED STATES PATENT AND TRADEMARK OFFICE
CERTIFICATE OF CORRECTION

| | | |
|---|---|---|
| PATENT NO. | : 6,297,037 B1 | Page 1 of 1 |
| DATED | : October 2, 2001 | |
| INVENTOR(S) | : Christopher C. Barnett, Colin Mitchinson, Scott D. Power and Carol A. Requadt | |

It is certified that error appears in the above-identified patent and that said Letters Patent is hereby corrected as shown below:

<u>Column 65,</u>
Line 7, insert word -- in -- before the word "*Bacillus.*"

Signed and Sealed this

Third Day of December, 2002

JAMES E. ROGAN
*Director of the United States Patent and Trademark Office*